(12) United States Patent
Harlev et al.

(10) Patent No.: US 10,335,051 B2
(45) Date of Patent: *Jul. 2, 2019

(54) BEAT ALIGNMENT AND SELECTION FOR CARDIAC MAPPING

(71) Applicant: Rhythmia Medical, Inc., Burlington, MA (US)

(72) Inventors: Doron Harlev, Brookline, MA (US); Rotem Eldar, Cambridge, MA (US)

(73) Assignee: Rhythmia Medical, Inc., Burlington, MA (US)

( * ) Notice: Subject to any disclaimer, the term of this patent is extended or adjusted under 35 U.S.C. 154(b) by 760 days.

This patent is subject to a terminal disclaimer.

(21) Appl. No.: 14/679,832

(22) Filed: Apr. 6, 2015

(65) Prior Publication Data
US 2015/0282729 A1 Oct. 8, 2015

Related U.S. Application Data

(63) Continuation of application No. 13/243,401, filed on Sep. 23, 2011, now Pat. No. 9,002,442.
(Continued)

(51) Int. Cl.
*A61B 5/04* (2006.01)
*A61B 5/00* (2006.01)
(Continued)

(52) U.S. Cl.
CPC ........ *A61B 5/04012* (2013.01); *A61B 5/0402* (2013.01); *A61B 5/042* (2013.01);
(Continued)

(58) Field of Classification Search
CPC ... A61B 5/04012; A61B 5/0402; A61B 5/042; A61B 5/0422; A61B 5/04525; A61B 5/6852; A61B 5/7246
(Continued)

(56) References Cited

U.S. PATENT DOCUMENTS 1,674,518 A   6/1928   Parsons
2,939,309 A   6/1960   Sitton
(Continued)

FOREIGN PATENT DOCUMENTS

EP   2663227 A1   11/2013
JP   H09508293 A   8/1997
(Continued)

OTHER PUBLICATIONS

Authorized officer Blaine R. Copenheaver, International Search Report/Written Opinion in PCT/US2012/020935 dated May 8, 2012, 30 pages.
(Continued)

*Primary Examiner* — Christopher Koharski
*Assistant Examiner* — Pamela M. Bays

(57) ABSTRACT

A method including measuring cardiac beats in signals at one or more electrodes on a catheter in response to electrical activity in the heart cavity and collecting a plurality of additional data signals related to the cardiac beats, computing criteria that is used to characterize beat morphology of a cardiac beat in the plurality of additional data signals, the criteria based on a comparison of the plurality of additional data signals and a beat template, selecting a subset of less than all of the cardiac beats in the signals measured by the one or more electrodes by determining, based on the criteria, whether to select the cardiac beat and include beat data for the cardiac beat, and determining physiological information based on the selected subset of less than all of the cardiac beats in the signals measured by the one or more electrodes.

12 Claims, 8 Drawing Sheets

Related U.S. Application Data

(60) Provisional application No. 61/432,386, filed on Jan. 13, 2011.

(51) Int. Cl.
    *A61B 5/042*     (2006.01)
    *A61B 5/0402*     (2006.01)
    *A61B 5/0452*     (2006.01)

(52) U.S. Cl.
    CPC ........ *A61B 5/04525* (2013.01); *A61B 5/6852* (2013.01); *A61B 5/7246* (2013.01); *A61B 5/0422* (2013.01); *A61B 5/7285* (2013.01)

(58) Field of Classification Search
    USPC ...................................................... 600/509
    See application file for complete search history.

(56) References Cited

U.S. PATENT DOCUMENTS

| | | | |
|---|---|---|---|
| 4,649,924 | A | 3/1987 | Taccardi |
| 4,674,518 | A | 6/1987 | Salo |
| 4,840,182 | A | 6/1989 | Carlson |
| 4,920,490 | A | 4/1990 | Isaacson |
| 4,964,410 | A | 10/1990 | Leahey et al. |
| 5,156,151 | A | 10/1992 | Imran |
| 5,284,142 | A | 2/1994 | Goble et al. |
| 5,297,549 | A | 3/1994 | Beatty et al. |
| 5,300,068 | A | 4/1994 | Rosar et al. |
| 5,341,807 | A | 8/1994 | Nardella |
| 5,381,333 | A | 1/1995 | Isaacson et al. |
| 5,469,858 | A | 11/1995 | Osborne |
| 5,480,422 | A | 1/1996 | Ben-Haim |
| 5,500,011 | A | 3/1996 | Desai |
| 5,553,611 | A | 9/1996 | Budd et al. |
| 5,568,809 | A | 10/1996 | Ben-Haim |
| 5,577,502 | A | 11/1996 | Darrow et al. |
| 5,588,429 | A | 12/1996 | Isaacson et al. |
| 5,634,469 | A | 6/1997 | Bruder et al. |
| 5,662,108 | A | 9/1997 | Budd et al. |
| 5,687,737 | A | 11/1997 | Branham et al. |
| 5,697,377 | A | 12/1997 | Wittkampf |
| 5,704,365 | A | 1/1998 | Albrecht et al. |
| 5,711,305 | A | 1/1998 | Swanson et al. |
| 5,722,402 | A | 3/1998 | Swanson et al. |
| 5,724,985 | A | 3/1998 | Snell et al. |
| 5,810,740 | A | 9/1998 | Paisner |
| 5,840,025 | A | 11/1998 | Ben-Haim |
| 5,840,031 | A | 11/1998 | Crowley |
| 5,846,198 | A | 12/1998 | Killmann |
| 5,848,972 | A | 12/1998 | Triedman et al. |
| 5,921,982 | A | 7/1999 | Lesh et al. |
| 5,954,665 | A | 9/1999 | Ben-Haim |
| 5,971,933 | A | 10/1999 | Gopakumaran et al. |
| 5,983,126 | A | 11/1999 | Wittkampf |
| 6,014,581 | A | 1/2000 | Whayne et al. |
| 6,050,267 | A | 4/2000 | Nardella et al. |
| 6,095,150 | A | 8/2000 | Panescu et al. |
| 6,167,296 | A | 12/2000 | Shahidi |
| 6,226,542 | B1 | 5/2001 | Reisfeld |
| 6,236,883 | B1 | 5/2001 | Ciaccio et al. |
| 6,236,886 | B1 | 5/2001 | Cherepenin et al. |
| 6,240,307 | B1 | 5/2001 | Beatty et al. |
| 6,246,898 | B1 | 6/2001 | Vesely et al. |
| 6,254,536 | B1 | 7/2001 | DeVito |
| 6,278,894 | B1 | 8/2001 | Salo et al. |
| 6,298,257 | B1 | 10/2001 | Hall et al. |
| 6,308,093 | B1 | 10/2001 | Armoundas et al. |
| 6,314,310 | B1 | 11/2001 | Ben-Haim et al. |
| 6,317,619 | B1 | 11/2001 | Boernert et al. |
| 6,318,375 | B1 | 11/2001 | Plicchi et al. |
| 6,360,123 | B1 | 3/2002 | Kimchi et al. |
| 6,368,285 | B1 | 4/2002 | Osadchy et al. |
| 6,400,981 | B1 | 6/2002 | Govari |
| 6,516,807 | B1 | 2/2003 | Panescu et al. |
| 6,547,082 | B1 | 4/2003 | Babini |
| 6,556,695 | B1 | 4/2003 | Packer et al. |
| 6,574,492 | B1 | 6/2003 | Ben-Haim et al. |
| 6,574,498 | B1 | 6/2003 | Gilboa |
| 6,593,884 | B1 | 7/2003 | Gilboa et al. |
| 6,599,241 | B1 | 7/2003 | Murphy |
| 6,600,948 | B2 | 7/2003 | Ben-Haim et al. |
| 6,603,996 | B1 | 8/2003 | Beatty et al. |
| 6,631,290 | B1 | 10/2003 | Guck et al. |
| 6,640,119 | B1 | 10/2003 | Budd et al. |
| 6,650,927 | B1 | 11/2003 | Keidar |
| 6,690,963 | B2 | 2/2004 | Ben-Haim et al. |
| 6,701,176 | B1 | 3/2004 | Halperin et al. |
| 6,728,562 | B1 | 4/2004 | Budd et al. |
| 6,773,402 | B2 | 8/2004 | Govari et al. |
| 6,807,439 | B2 | 10/2004 | Edwards et al. |
| 6,839,588 | B1 | 1/2005 | Rudy |
| 6,847,839 | B2 | 1/2005 | Ciaccio et al. |
| 6,872,428 | B2 | 3/2005 | Yang et al. |
| 6,892,090 | B2 | 5/2005 | Verard et al. |
| 6,892,091 | B1 | 5/2005 | Ben-Haim et al. |
| 6,939,309 | B1 | 9/2005 | Beatty et al. |
| 6,957,101 | B2 | 10/2005 | Porath et al. |
| 6,978,168 | B2 | 12/2005 | Beatty et al. |
| 6,990,370 | B1 | 1/2006 | Beatty et al. |
| 7,016,719 | B2 | 3/2006 | Rudy et al. |
| 7,043,292 | B2 | 5/2006 | Tarjan et al. |
| 7,263,397 | B2 | 8/2007 | Hauck et al. |
| 7,505,810 | B2 | 3/2009 | Harlev et al. |
| 7,515,954 | B2 | 4/2009 | Harlev et al. |
| 7,599,730 | B2 | 10/2009 | Hunter et al. |
| 7,706,867 | B1 | 4/2010 | Ostrow |
| 7,709,867 | B2 | 5/2010 | Ishikawa et al. |
| 7,729,752 | B2 | 6/2010 | Harlev et al. |
| 7,856,260 | B1 | 12/2010 | Ryu |
| 8,021,361 | B2 | 9/2011 | Paul et al. |
| 8,103,327 | B2 | 1/2012 | Harlev et al. |
| 8,103,338 | B2 | 1/2012 | Harlev et al. |
| 8,137,343 | B2 | 3/2012 | Harlev et al. |
| 8,182,433 | B2 | 5/2012 | Leo et al. |
| 8,267,926 | B2 | 9/2012 | Paul et al. |
| 8,357,152 | B2 | 1/2013 | Govari et al. |
| 8,428,700 | B2 | 4/2013 | Harlev et al. |
| 8,948,837 | B2 | 2/2015 | Harlev et al. |
| 9,002,442 | B2 | 4/2015 | Harley et al. |
| 9,107,599 | B2 | 8/2015 | Harlev et al. |
| 9,277,872 | B2 | 3/2016 | Harlev et al. |
| 9,289,148 | B2 | 3/2016 | Harlev et al. |
| 2002/0091333 | A1 | 7/2002 | Hsu et al. |
| 2002/0115941 | A1 | 8/2002 | Whayne et al. |
| 2002/0151807 | A1 | 10/2002 | Goldin |
| 2002/0177421 | A1 | 11/2002 | Muhammad et al. |
| 2003/0018251 | A1 | 1/2003 | Solomon |
| 2003/0065271 | A1 | 4/2003 | Khoury |
| 2003/0076277 | A1 | 4/2003 | Muramatsu et al. |
| 2003/0078509 | A1 | 4/2003 | Panescu |
| 2003/0216630 | A1 | 11/2003 | Jersey-Willuhn et al. |
| 2004/0039293 | A1 | 2/2004 | Porath et al. |
| 2004/0077942 | A1 | 4/2004 | Hall et al. |
| 2004/0097806 | A1 | 5/2004 | Hunter et al. |
| 2004/0127805 | A1 | 7/2004 | MacAdam et al. |
| 2004/0243015 | A1 | 12/2004 | Smith et al. |
| 2004/0254437 | A1 | 12/2004 | Hauck et al. |
| 2005/0038337 | A1 | 2/2005 | Edwards |
| 2005/0054918 | A1 | 3/2005 | Sra |
| 2005/0107834 | A1 | 5/2005 | Freeman et al. |
| 2005/0154282 | A1 | 7/2005 | Li et al. |
| 2005/0288599 | A1 | 12/2005 | MacAdam et al. |
| 2006/0085049 | A1 | 4/2006 | Cory et al. |
| 2006/0116575 | A1 | 6/2006 | Willis |
| 2006/0122526 | A1 | 6/2006 | Berenfeld et al. |
| 2006/0178587 | A1 | 8/2006 | Khoury |
| 2006/0200049 | A1 | 9/2006 | Leo et al. |
| 2006/0241401 | A1 | 10/2006 | Govari et al. |
| 2007/0016007 | A1 | 1/2007 | Govari et al. |
| 2007/0038078 | A1 | 2/2007 | Osadchy |
| 2007/0049821 | A1 | 3/2007 | Willis |
| 2007/0073179 | A1 | 3/2007 | Afonso et al. |
| 2007/0083193 | A1 | 4/2007 | Werneth et al. |

(56) References Cited

U.S. PATENT DOCUMENTS

| | | | |
|---|---|---|---|
| 2007/0100332 A1 | 5/2007 | Paul et al. | |
| 2007/0197929 A1 | 8/2007 | Porath et al. | |
| 2007/0265539 A1 | 11/2007 | Hastings et al. | |
| 2007/0270703 A1 | 11/2007 | He et al. | |
| 2007/0287902 A1 | 12/2007 | Fuimaono et al. | |
| 2007/0299351 A1* | 12/2007 | Harlev | A61B 5/0422 600/509 |
| 2007/0299352 A1 | 12/2007 | Harlev et al. | |
| 2008/0137927 A1 | 6/2008 | Altmann et al. | |
| 2008/0190438 A1 | 8/2008 | Harlev et al. | |
| 2008/0221566 A1 | 9/2008 | Krishnan | |
| 2008/0234588 A1 | 9/2008 | Feldman et al. | |
| 2008/0249424 A1 | 10/2008 | Harlev et al. | |
| 2008/0281319 A1 | 11/2008 | Paul et al. | |
| 2009/0069642 A1 | 3/2009 | Gao et al. | |
| 2009/0069704 A1 | 3/2009 | MacAdam et al. | |
| 2009/0093806 A1 | 4/2009 | Govari et al. | |
| 2009/0099468 A1* | 4/2009 | Thiagalingam | A61B 5/0452 600/515 |
| 2009/0171274 A1 | 7/2009 | Harlev et al. | |
| 2009/0177072 A1 | 7/2009 | Harlev et al. | |
| 2009/0253976 A1 | 10/2009 | Harlev et al. | |
| 2009/0264767 A1 | 10/2009 | Griffin et al. | |
| 2009/0281439 A1 | 11/2009 | Harlev et al. | |
| 2010/0049069 A1 | 2/2010 | Tarassenko et al. | |
| 2010/0168620 A1 | 7/2010 | Klimovitch et al. | |
| 2010/0274150 A1 | 10/2010 | Harlev et al. | |
| 2010/0286550 A1 | 11/2010 | Harlev et al. | |
| 2010/0286551 A1 | 11/2010 | Harlev et al. | |
| 2010/0311482 A1 | 12/2010 | Lange | |
| 2012/0184684 A1 | 7/2012 | Funk et al. | |
| 2012/0184858 A1 | 7/2012 | Harlev et al. | |
| 2012/0184865 A1 | 7/2012 | Harlev et al. | |
| 2015/0112178 A1 | 4/2015 | Harlev et al. | |
| 2016/0051160 A1 | 2/2016 | Harlev et al. | |

FOREIGN PATENT DOCUMENTS

| | | |
|---|---|---|
| JP | H10234693 A | 9/1998 |
| JP | 2001070269 A | 3/2001 |
| JP | 2005506097 A | 3/2005 |
| JP | 2005131367 A | 5/2005 |
| JP | 2007537823 A | 12/2007 |
| JP | 2008536633 A | 9/2008 |
| JP | 2009537252 A | 10/2009 |
| JP | 2009539566 A | 11/2009 |
| WO | 2005115232 A1 | 12/2005 |
| WO | 2006113698 A1 | 10/2006 |
| WO | 2007137077 A2 | 11/2007 |
| WO | 2010020958 A1 | 2/2010 |
| WO | 2012097067 A1 | 7/2012 |

OTHER PUBLICATIONS

International Preliminary Report on Patentability, PCT/US2012/020935, dated Jul. 25, 2013, 24 pages.
Ju et al., "Mean value coordinates for closed triangular meshes," ACM Trans. Graph. 24(3):561-566 (2005).
McLeish et al., "A Study of the Motion and Deformation of the Heart Due to Respiration," IEEE Transactions on Medical Imaging, 21(9):1142-1150 (2002).
U.S. Appl. No. 13/182,825, Harlev et al., filed Jul. 14, 2011.
U.S. Appl. No. 13/182,830, Harlev et al., filed Jul. 14, 2011.
U.S. Appl. No. 61/432,404, Harlev et al., filed Jan. 13, 2011.
Solomon et al., "Real-Time Cardiac Catheter Navigation on Three-Dimensional CT Images", Journal of Interventional Cardiac Electrophysiology, 8:27-36, 2003.
Sra et al., "Registration of Three-Dimensional Left Atrial Computed Tomographic Images With Projection Images Obtained Using Fluoroscopy", Circulation, 112:3763-3768, 2005.
Sra, Jasbir et al, "Registration of 3D Computed Tomographic Images With Interventional Systems: Implications for Catheter Ablation of Atrial Fibrillation", J Intery Card Electrophysiol, 16:141-148, 2006.
Stevenson, "Radiofrequency Catheter Ablation of Ventricular Tachycardia After Myocardial Infarction", Circulation, 98:308-314, 1998.
Taccardi et al., "A New Intracavitary Probe for Detecting the Site of the Origin of Ectopic Ventricular Beats During One Cardiac Cycle", Circulation, 75(1):272-281, 1987.
Thal et al., "Novel Applications in Catheter Ablation", Journal of Interventional Cardiac Electrophysiology, 13:17-21, 2005.
Thiagalingam et al., "Noncontact Mapping of the Left Ventricle: Insights from Validation With Transmural Contact Mapping", PACE, 27:570-578, 2004.
Voth, "The Inverse Problem of Electrocardiography: Industrial Solutions and Simulations", BEM and NFSI Conference Proceedings, Minneapolis, MN, May 12-15, 2005, pp. 191-194.
Wittkampf et al., "LocaLisa: New Technique for Real-Time 3-Dimensional Localization of Regular Intracardiac Electrodes", Circulation, 99:1312-1317, 1999.
Yezzi, Anthony et al., "A Geometric Snake Model for Segmentation", IEEE Transactions on Medical Imaging, 16(2) Apr. 1997.
Invitation to Pay Additional Fees, and, Where Applicable, Protest Fee issued in PCT/US2016/053627, dated Dec. 21, 2016, 8 pages.
International Search Report and Written Opinion issued in PCT/US2016/053627, dated Feb. 14, 2017, 17 pages.
Adams et al., "Seeded Region Growing", IEEE Transactions on Pattern Analysis and Machine Intelligence, 16(6):641-647, 1994.
Arthur, "Clinical Use of Intracardiac Impedance: Current Applications and Future Perspectives", PACE, vol. 24:500-506, Apr. 2001.
Authorized officer Carl H. Layno, International Search Report and the Written Opinion in PCT/US07/70854 dated Sep. 12, 2008, 15 pages.
Authorized officer Lee W. Young, International Search Report and the Written Opinion in PCT/US08/52385 dated Aug. 8, 2008, 11 pages.
Authorized officer, Blaine R. Copenheaver, International Search Report and the Written Opinion in PCT/US2009/061277 dated Apr. 8, 2010, 13 pages.
Baan, Jan et al., "Continuous Measurement of Left Ventricular Volume In Animals and Humans by Conductance Catheter", Circulation, 07(5):812-823, 1984.
Badics, "Real-Time Reconstruction of Endocardial Potential Maps in Non-Contact Cardiace Mapping", International Journal for computation and Mathematics in Electrical Engineering (COMPEL), vol. 28, No. 4, 2009.
Ben-Haim et al., "Nonfluoroscopic, in Vivo Navigation and Mapping Technology", Nature Medicine, 2(12):1393-1395, 1996.
Besi et al., "A Method for Registration of 3-D Shapes", IEEE Transaction on Pattern Analysis and Machine Intelligence, 14(2):239-256, 1992.
Blomstrom-Lundqvist et al., "ACC/AHA/ESC Guidelines for the Management of Patients with Supraventricular Arrhythmias-Executive Summary", Journal of the American College of Cardiology, 42(8):1493-1531, 2003.
Breithardt et al., "AHA Medical/Scientific Statement—Special Report: Standards for Analysis of Ventricular Late Potentials Using High-Resolution or Signal/Averaged Electrocardiography", Circulation, 83(4):1481-1488, 1991.
Brooks et al., "Electrical Imaging of the Heart", IEEE Signal Processing Magazine, pp. 24-42, 1997.
Caspi et al., "Stem Cell Research: Regenerating the Heart Using Human Embryonic Stem Cells—from Cell to Bedside", IMAJ 8:208-214, 2006.
De Groot et al., "Three-Dimensional Catheter Positioning During Radiofrequency Ablation in Patients: First Application of a Real-Time Position Management System", Journal of Cardiovascular Electrophysiology, 11:1183-1192, 2000.
Donahue et al., "Focal Modification of Electrical Conduction in the Heart by Viral Gene Transfer", Nature Medcine, 6 (12):(1395-1398, 2000.
Dong et al., "Integrated Electroanatornic Mapping With Three-Dimensional Computed Tomographic Images for Real-Time Guided Ablations", Circulation 113:186-194, 2006.

(56) References Cited

OTHER PUBLICATIONS

Durrer et al., "Total Excitation of the Isolated Human Heart", Circulation, XL1:899-912, 1970.
Ector, Joris et al., "Cardiac Three-Dimensional Magnetic Resonance Imaging and Fluoroscopy Merging", Circulation, 112:3769-3776, 2005.
Friedman, "Catheter Cryoablation of Cardiac Arrhythmias", Current Opinion in Cardiology, 20:48-54, 2005.
Friedman, "Novel Mapping Techniques for Cardiac Electrophysiology", Heart, 87:575-582, 2002.
Gepstein et al., "A Novel Method for Nonfluoroscopic Catheter-Based Electroanatomical Mapping of the Heart", Circulation 95:1611-1622, 1997.
Huang, Yi-Chih et al., "Development of a Third Generation Intraventricular Impedance Imaging (Iii) System Evaluation of Hardware Design", Engineering in Medicine and Biology Society, Proceedings of the 19th Annual Internal Conference of the IEEE/EMBS, 6:2442-2444 Oct. 30-Nov. 2, 1997.
Jain et al., "Cell Therapy Attenuates Deleterious Ventricular Remodeling and Improves Cardiac Performance after Myocardial Infarction", Circulation, 103:1920-1927, 2001.
Jalife, "Rotors and Spiral Waves in Atrial Fibrillation", Journal of Cardiovascular Electrophysiology, 14:776-780, 2003.
Jane et al., Alignment Methods for Averaging of High-Resolution Cardiac Signals: A Comparative Study of Performance, IEEE Transaction on Biomedical Engineering, 38(6):571-579, 1991.
Jia et al., "Electrophysiologic Endocardial Mapping from a Noncontact Nonexpandable Catheter: A Validation Study of a Geometry-Based Concept". Journal of Cardiovascular Electrophysiology, 11:1238-1251, 2000.
Kikuchi et al., "Targeted Modification of Atrial Electrophysiology by Homogeneous Transmural Artial Gene Transfer", Circulation, 111:264-270, 2005.
Kistler et al., "Validation of Three-Dimensional Cardiac Image Integration: Use of Integrated CT Image into Electroanatomic Mapping System to Performa Catheter Ablation of Atrial Fibrillation", Journal of Cardiovascular Electrophysiology, 17:341-348, 2006.
Kun, Stevan et al., "Conductance Volumetric Model of an Eccentrically Positioned Catheter within a Three-Compartment Ellipsoidal Ventricle", U, IEEE Transactions on Jun. 1993, 40(6); 589-592.
Laciar et al., "Improved Alignment Method for Noisy High-Resolution ECG and Holter Records Using Multiscale Cross-Correlation", IEEE Transactions on Biomedical Engineering, 50(3):344-353, 2003.
Liu et al., "Endocardial Potential Mapping from a Noncontact Nonexpandable Catheter: A Feasibility Study", Annals of Biomedical Engineering, 26:994-1009, 1998.
Lorensen et al., "Marching Cubes: A High Resolution 3D Surface Construction Algorithm", Computer Graphics 21(4):163-169, Jul. 1987.
Makela et al., "A Review of Cardiac Image Registration Methods", IEEE Transaction on Medical Imaging, 21(9):1011-1021, 2002.
Malladi, R. et al., "A Geometric Approach to Segmentation and Analysis of 3D Medical Images", Mathematical Methods in Biomedical Image Analysis, Proceedings of the Workshop on, Jun. 21-22, 1996, pp. 244-252.
Mangan, Alan et al., "Partitioning 3D Surface Meshes Using Watershed Segmentation", IEEE Transactions on Visualization and Computer Graphics, 5(4):308-321, 1999.

Meininger et al., "Initial Experience with a Novel Focused Ultrasound Ablation System for Ring Ablation Outside the Pulmonary Vein", Journal of Interventional Cardiac Electrophysiology, 8:141-148, 2003.
Merrill, Daniel R. et al., "Electrical stimulation of excitable tissue: design of efficacious and safe protocols", Journal of Neuroscience Methods, 141:171-198, 2005.
Miller, "Editor's Forum—Application of Registration for Ablation: A Marriage of Technologies", Journal of Interventional Cardiac Electrophysiology, 11:87-89, 2004.
Nademanee et al., "A New Approach for Catheter Ablation of Atrial Fibrillation: Mapping of the Electrophysiologic Substrate", Journal of the American College of Cardiology, 43(11):2044-2053, 2004.
Noseworthy et al., "The Impact of Respiration on Left Atrial and Pulmonary Venous Anatomy: Implications for Image-Guided Intervention", Heart Rhythm, 2:1173-1178, 2005.
Pappose et al., "Robotic Magnetic Navigation for Atrial Fibrillation Ablation", Journal of the American College of Cardiology, 47(7): 1390-1400, 2006.
Paragios, "A Level Set Approach for Shape-Driven Segmentation and Tracking of the Left Ventricle", IEEE Transactions on Medical Imaging, 22(6):773-776, 2003.
Persson et al., "A Simple Mesh Generator in MATLAB", SIAM Review, 46(2):329-345, 2004.
Pham, Dzung, et al., "Current Methods in Medical Image Segmentation", Annu. Rev. Biomed, Eng., 02:315-337, 2000.
Rao et al., "Novel Noncontact Catheter System for Endocardial Electrical and Anatomical Imaging", Annals of Biomedical Engineering, 32(4):573-584, 2004.
Reddy et al., "Use of a Diode Laser Balloon Ablation Catheter to Generate Circumferential Pulmonary Venous Lesions in an Open-Thoracotomy Caprine Model", PACE, 27:52-57, 2004.
Reddy et al., "Integration of Cardiac Meagnetic Resonance Imaging with Three-Dimentional Electroanatomic Mapping to Guide Left Ventricular Catheter Manipulation—Feasibility is a Porcine Modelof Healed Myocardial Infarction", Journal of the American College of Cardiology, 44(11):2202-2213, 2004.
Sanders et al., "Spectral Analysis Identifies Sites of High-Frequency Activity Maintaining Atrial Fibrillation in Humans", Circulation, 112:789-797, 2005.
Sethian, "Level Set Methods and Fast Marching Methods: Evolving Interfaces in Computational Geometry, Fluid Mechanics, Computer Vision, and Materials Science", Department of Mathematics-University of California, Berkeley, Cambridge University Press, 1999.
Smits et al., "Catheter-Based Intramyocarial Injection of Autologous Skeletal Myoblasts as a Primary Treatment of Ischemic Heart Failure", Journal of the American College of Cardiology, 42(12):2063-2069, 2003.
Extended International Search Report issued in European application 12733844.0, dated Jun. 26, 2017, 9 pages.
Extended International Search Report issued in European Application 12734224.4, dated Jun. 27, 2017, 10 pages.
Kriebel et al., "Noncontact Mapping and Radiofrequency Catheter Ablation of Fast and Hemodynamically Unstable Ventricular Tachycardia After Surgical Repair of Tetralogy of Fallot", Journal of the American College of Cardiology, Elsevier, New York, NY, vol. 50, No. 22, Nov. 13, 2007, pp. 2162-2168.
Martin K. Stiles et al., "The Effect of Electrogram Duration on Quantification of Complex Fractionated Atrial Electrograms and Dominant Frequency", Journal of Cardiovascular Electrophysiology, vol. 19, No. 3, Mar. 1, 2008, pp. 252-258.
Wazni et al., "Atrial Arrhythmias After Surgical Maze", Journal of the American College of Cardiology, Elsevier, New York, NY, vol. 48, No. 7, Oct. 3, 2006, pp. 1405-1409.

\* cited by examiner

US 10,335,051 B2

BEAT ALIGNMENT AND SELECTION FOR CARDIAC MAPPING

CROSS-REFERENCE TO RELATED APPLICATION

This application is a continuation application of U.S. application Ser. No. 13/243,401, filed on Sep. 23, 2011, now U.S. Pat. No. 9,002,442, which claims priority to U.S. Provisional Application 61/432,386, filed on Jan. 13, 2011, both of which are hereby incorporated by reference in their entirety.

TECHNICAL FIELD

This invention relates to the determination and representation of physiological information relating to a heart surface.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart (e.g., based on cardiac signals), such as at various locations on the endocardium surface ("cardiac mapping"), to identify the site of origin of the arrhythmia followed by a targeted ablation of the site. To perform such cardiac mapping a catheter with one or more electrodes can be inserted into the patient's heart chamber.

Conventional 3D mapping techniques include contact mapping and non-contact mapping. In contact mapping techniques one or more catheters are advanced into the heart. Physiological signals resulting from the electrical activity of the heart are acquired with one or more electrodes located at the catheter distal tip after determining that the tip is in stable and steady contact with the endocardium surface of a particular heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm. On the other hand, in non-contact-based mapping systems a multiple electrode catheter is percutaneously placed in the heart chamber of interest. Once in the chamber, the catheter is deployed to assume a 3D shape. Using the signals detected by the non-contact electrodes and information on chamber anatomy and relative electrode location, the system provides physiological information regarding the endocardium of the heart chamber.

SUMMARY

In some aspects, a method includes inserting a catheter into a heart cavity, the catheter comprising one or more electrodes and moving the catheter to each of multiple, different positions in the heart cavity. The method also includes, for each of the different catheter positions, concurrently measuring signals at the catheter electrodes in response to electrical activity in the heart cavity and collecting a plurality of additional data signals. The method also includes defining a template set comprising of the plurality of additional data signals collected during an exemplary beat of interest, computing criteria for each of the plurality of additional data signals based on a comparison of the plurality of additional data signals and the template set, and synchronizing the signals measured at the different catheter positions with one another according to a heart beat cycle by calculating a single synchronization offset based on the plurality of the computed criteria. The method also includes determining physiological information at multiple locations of the endocardium surface based on the measured signals at the different catheter positions by processing the synchronized signals.

Embodiments can include one or more of the following.

Computing the criteria can include computing a correlation of each of the plurality of additional data signals to the corresponding signal templates. The correlation can be a cross-correlation.

Processing the synchronized signals can include processing the synchronized signals as though they were obtained at one time.

Synchronizing the signals can include aligning the signals measured at the different catheter positions relative to a phase in an electrical cycle of the heart.

The method can also include generating the template representing an exemplary beat of interest.

Synchronizing the signals can include aligning the plurality of additional data signals with the templates representing the exemplary beat of interest. Aligning the plurality of additional data signals with the templates representing the exemplary beat of interest can include computing a cross-correlation to align the template and the data signals.

The plurality of additional data signals can be multiple physiological data signals. Computing the criteria based on the comparison of the plurality of additional data signals and the corresponding signal templates can include, for each of the additional data signals, aligning the template and the additional data signal using a cross-correlation calculation to generate a time offset factor. Synchronizing the signals can include averaging the time offset factors for each of the cross-correlation calculations to determine an average time offset factor.

The plurality of additional data signals can be multiple ECG signals. The plurality of additional data signals can include at least one ECG signal and at least one intercardiac electrogram signal. The plurality of additional data signals can include a cardiac pacing signal and at least one physiological data signal.

The method can also include defining additional template sets of the plurality of additional data signals collected during different exemplary beats of interest.

Computing criteria for each of the plurality of additional data signals based on a comparison of the plurality of additional data signals and the template set can include computing criteria for each of the plurality of additional data signals based on a comparison of the plurality of additional data signals and the template set and the additional template sets.

The method can also include grouping the signals measured at the different catheter positions based on the computed criteria for the template set and each of the additional template sets.

Determining the physiological information can include processing each group of measured signals separately. Determining the physiological information can include determining the physiological information based at least in part on a mathematical operator approximating Laplace's equation.

The method can also include displaying at least a portion of the determined physiological information.

The physiological information can be electrical information.

The method can also include using the determined physiological information to guide treatment of the heart cavity. The treatment can include ablation of one or more selected regions of the heart.

The method can also include repeating the measurement of catheter electrode signals and the determination of the physiological information after the ablation treatment. The treatment can include cell therapy, gene therapy, or the application of other biological agents.

The determination of the physiological information at the multiple locations of the endocardium surface can also include applying a transformation function to the synchronized signals, wherein the transformation function relates signals measured from at least some of the different positions of the catheter in the heart cavity to the physiological information at the multiple locations of the endocardium surface.

The determination of the physiological information at the multiple locations of the endocardium surface can also include determining the transformation function by calculating a forward transformation for relating the physiological information at the multiple locations of the endocardium surface to the signals measured for the different positions of the catheter in the heart cavity and inverting the forward transformation. The inverting can include reformulating an underdetermined matrix inversion by regularization. The inverting can also include a least squares minimization.

The method can also include selecting a subset of less than all of the signals measured by the electrodes based on the computed criteria related to the plurality of additional data signals; and determining physiological information can include processing the selected subset of signals measured by the electrodes.

The plurality of additional data signals can include a plurality of physiological data signals. The computed criteria can include a value representing a similarity between the plurality of additional data signals and the signal templates.

The method can also include selecting a subset of less than all of the signals by comparing the value with a threshold value and including the signals in the subset for the beat if the value is greater than the threshold value. The value can be a correlation value. The value can be a binary value.

Selecting a subset of less than all of the signals can include determining whether to include the signals for a cardiac beat in the subset of less than all of the synchronized signals based on the computed criteria. The method can also include averaging the computed criteria for at least some of the additional data signals and comparing the averaged criteria results to a threshold.

The method can also include averaging the computed criteria for a subset of less than all of the computed criteria and comparing the averaged criteria results to a threshold.

Selecting the subset of less than all of the synchronized signals can include comparing beat duration information for a beat with an expected beat duration and excluding the signals from the subset of less than all of the synchronized signals if the beat duration is above or below a threshold. Selecting the subset of less than all of the synchronized signals can include comparing an energy for a beat with an expected energy and excluding the signals from the subset of less than all of the synchronized signals if the energy is above or below a threshold. Selecting the subset of less than all of the synchronized signals can include selecting signals based on a location of the heart beat in a beat train of a morphology of interest. Selecting the subset of less than all of the synchronized signals based on the location of the heart beat in the beat train can include excluding the signals from the subset of less than all of the synchronized signals if the heart beat is the first heart beat in the beat train. Selecting the subset of less than all of the synchronized signals can include selecting signals based on a respiration phase. Selecting the subset of less than all of the synchronized signals can include selecting signals based on the mechanical structure of the cardiac chamber. Selecting the subset of less than all of the synchronized signals can include selecting signals based on a phase of respiration.

In some aspects, a system includes one or more electrodes configured to measure signals in response to electrical activity in a heart cavity having a surface, one or more additional devices configured to measure additional data signals, and a processing unit. The processing unit is configured to define a template set comprising of the plurality of additional data signals collected during an exemplary beat of interest, compute criteria for each of the plurality of additional data signals based on a comparison of the plurality of additional data signals and the template set, synchronize the signals measured at the different catheter positions with one another according to a heart beat cycle by calculating a single synchronization offset based on the plurality of the computed criteria, and determine physiological information at multiple locations of the endocardium surface based on the measured signals at the different catheter positions by processing the synchronized signals.

Embodiments can include one or more of the following.

The processing unit can be configured to compute a correlation of each of the plurality of additional data signals to the corresponding signal templates. The correlation can be a cross-correlation.

The processing unit can be configured to process the synchronized signals as though they were obtained at one time. The processing unit can be configured to align the signals measured at the different catheter positions relative to a phase in an electrical cycle of the heart. The processing unit can be configured to align the plurality of additional data signals with the templates representing the exemplary beat of interest. The configurations to align the plurality of additional data signals with the templates representing the exemplary beat of interest can include configurations to compute a cross-correlation to align the template and the data signals.

The plurality of additional data signals can be multiple physiological data signals. The plurality of additional data signals can include multiple ECG signals. The plurality of additional data signals can include at least one ECG signal and at least one intercardiac electrogram signal. The plurality of additional data signals can include a cardiac pacing signal and at least one physiological data signal.

The processing unit can be configured to define additional template sets of the plurality of additional data signals collected during different exemplary beats of interest. The processing unit can be configured to compute criteria for each of the plurality of additional data signals based on a comparison of the plurality of additional data signals and the template set and the additional template sets. The processing unit can be configured to group the signals measured at the different catheter positions based on the computed criteria for the template set and each of the additional template sets. The processing unit can be configured to determine the physiological information based at least in part on a mathematical operator approximating Laplace's equation. The processing unit can be configured to display at least a portion of the determined physiological information.

In some aspects, a method includes inserting a catheter into a heart cavity, the catheter comprising one or more electrodes, moving the catheter to each of multiple, different positions in the heart cavity, for each of the different catheter positions, concurrently measuring signals at the catheter electrodes in response to electrical activity in the heart cavity and collecting one or more additional data signals, selecting a subset of less than all of the signals measured by the electrodes based on a plurality of computed criteria related to the one or more additional data signals, and determining physiological information at multiple locations of the endocardium surface based on the subset of the signals measured by the electrodes at the different catheter positions by processing the subset of signals measured by the electrodes.

Embodiments can include one or more of the following.

The method can also include synchronizing the signals measured at the different catheter positions with one another based on the one or more additional data signals.

Selecting a subset of less than all of the measured signals can include selecting a subset of less than all of the synchronized measured signals. Processing the signals measured by the electrodes can include processing the signals measured by the electrodes as though they were obtained at one time. Selecting the subset of less than all of the signals can include comparing the one or more additional data signals for a beat with one or more templates representing an exemplary beat of interest.

The computed criteria can include a value representing a similarity between the one or more additional data signals for the beat and the one or more templates.

Selecting the subset of less than all of the signals can include comparing the generated value with a threshold value and including the signals in the subset for the beat if the value is greater than the threshold value. The value can be a correlation value. The value can be a binary value.

Selecting a subset of less than all of the signals can include collecting the one or more additional data signals from a plurality of channels, comparing each of the additional data signals from the plurality of channels to associated templates to generate comparison results, and determining whether to include the signals for a cardiac beat in the subset of less than all of the signals based on the comparison results.

The method can also include averaging the comparison results for at least some of the additional data signals and comparing the averaged comparison results to a threshold.

The method can also include averaging the comparison results for a subset of less than all of the comparison results and comparing the averaged comparison results to a threshold.

Selecting the subset of less than all of the synchronized signals can include comparing beat duration information for a beat with an expected beat duration and excluding the signals from the subset of less than all of the synchronized signals if the beat duration is below a threshold. Selecting the subset of less than all of the synchronized signals can include comparing an energy for a beat with an expected energy and excluding the signals from the subset of less than all of the synchronized signals if the energy is above a threshold. Selecting the subset of less than all of the synchronized signals can include selecting signals based on a location of the heart beat in a beat train of a morphology of interest. Selecting the subset of less than all of the synchronized signals based on the location of the heart beat in the beat train can include excluding the signals from the subset of less than all of the synchronized signals if the heart beat is the first heart beat in the beat train. Selecting the subset of less than all of the synchronized signals can include selecting signals based on a respiration phase. Selecting the subset of less than all of the synchronized signals can include selecting signals based on the mechanical structure of the cardiac chamber. Selecting the subset of less than all of the synchronized signals can include selecting signals based on a phase of respiration.

The method can also include displaying at least a portion of the determined physiological information.

The physiological information can be electrical information.

The method can also include using the determined physiological information to guide treatment of the heart cavity. The treatment can include ablation of one or more selected regions of the heart. The method can also include repeating the measurement of catheter electrode signals and the determination of the physiological information after the ablation treatment. The treatment can include cell therapy, gene therapy, or the application of other biological agents.

The determination of the physiological information at the multiple locations of the endocardium surface can include applying a transformation function to the synchronized signals. The transformation function can relate signals measured from at least some of the different positions of the catheter in the heart cavity to the physiological information at the multiple locations of the endocardium surface. The determination of the physiological information at the multiple locations of the endocardium surface can include determining the transformation function by calculating a forward transformation for relating the physiological information at the multiple locations of the endocardium surface to the signals measured for the different positions of the catheter in the heart cavity and inverting the forward transformation. The inverting can include reformulating an underdetermined matrix inversion by regularization. The inverting can include a least squares minimization.

The method can also include synchronizing the signals measured at the different catheter positions with one another according to a heart beat cycle by computing, for each of the measured signals, a criteria based on a comparison of the one or more additional data signals and a corresponding signal template representing an exemplary beat of interest. The method can also include generating the template representing an exemplary beat of interest. Synchronizing the signals can include aligning the additional data signal with the template representing the exemplary beat of interest. Aligning the additional data signal with the template representing the exemplary beat of interest can include computing a cross-correlation to align the template and the additional data signal.

The one or more additional data signals can include multiple physiological data signals. The one or more additional data signals can include multiple ECG signals. The one or more additional data signals can include at least one ECG signal and at least one intercardiac electrogram signal. The one or more additional data signals can include a cardiac pacing signal and at least one physiological data signal.

In some aspects, a system can include one or more electrodes configured to measure signals in response to electrical activity in a heart cavity having a surface and a processing unit configured to select a subset of less than all of the signals measured by the electrodes based on a plurality of computed criteria related to the one or more additional data signals and determine physiological information at multiple locations of the endocardium surface based on the subset of the signals measured by the electrodes at the different catheter positions by processing the subset of signals measured by the electrodes.

Embodiments can include one or more of the following.

The processing unit can be configured to synchronize the signals measured at the different catheter positions with one another based on the one or more additional data signals.

The processing unit can be configured to select a subset of less than all of the synchronized measured signals.

The processing unit can be configured to process the signals measured by the electrodes as though they were obtained at one time.

The processing unit can be configured to compare the one or more additional data signals for a beat with one or more templates representing an exemplary beat of interest. The computed criteria can include a value representing a similarity between the one or more additional data signals for the beat and the one or more templates.

The processing unit can be configured to compare the generated value with a threshold value and including the signals in the subset for the beat if the value is greater than the threshold value. The value can be a correlation value. The value can be a binary value.

The processing unit can be configured to collect the one or more additional data signals from a plurality of channels, compare each of the additional data signals from the plurality of channels to associated templates to generate comparison results, and determine whether to include the signals for a cardiac beat in the subset of less than all of the signals based on the comparison results.

The processing unit can be configured to average the comparison results for at least some of the additional data signals and compare the averaged comparison results to a threshold.

The processing unit can be configured to average the comparison results for a subset of less than all of the comparison results and compare the averaged comparison results to a threshold.

The processing unit can be configured to compare beat duration information for a beat with an expected beat duration and exclude the signals from the subset of less than all of the synchronized signals if the beat duration is below a threshold.

The processing unit can be configured to select the subset of less than all of the synchronized signals by comparing an energy for a beat with an expected energy and excluding the signals from the subset of less than all of the synchronized signals if the energy is above a threshold.

The processing unit can be configured to select the subset of less than all of the synchronized signals by selecting signals based on a location of the heart beat in a beat train of a morphology of interest.

The processing unit can be configured to select the subset of less than all of the synchronized signals based on the location of the heart beat in the beat train by excluding the signals from the subset of less than all of the synchronized signals if the heart beat is the first heart beat in the beat train. The processing unit can be configured to select the subset of less than all of the synchronized signals based on a respiration phase. The processing unit can be configured to select the subset of less than all of the synchronized signals based on the mechanical structure of the cardiac chamber. The processing unit can be configured to select the subset of less than all of the synchronized signals based on a phase of respiration. The processing unit can be configured to display at least a portion of the determined physiological information.

The physiological information can be electrical information.

In some aspects, a method includes inserting a catheter into a heart cavity, the catheter comprising one or more electrodes, moving the catheter to each of multiple, different positions in the heart cavity, for each of the different catheter positions, concurrently measuring signals at the catheter electrodes in response to electrical activity in the heart cavity and collecting one or more additional data signals, grouping the signals measured at the different catheter positions by computing, for each of the measured signals, a criteria based on a comparison of each of the one or more additional data signals to multiple corresponding signal templates to generate a plurality of groups of measured signals, the multiple signal templates representing multiple different exemplary beats of interest, and determining physiological information at multiple locations of the endocardium surface separately for each group of the measured signals by processing each group of measured signals separately. Determining the physiological information includes determining the physiological information based at least in part on a mathematical operator approximating Laplace's equation.

Embodiments can include one or more of the following.

Computing the criteria can include computing a correlation of each of the one or more additional data signals to the multiple corresponding signal templates. The correlation can be a cross-correlation.

Processing each group of signals separately can include processing the signals for each group as though they were obtained at one time. Grouping the signals can include selecting a first subset of less than all of the signals based on a comparison between the additional data signals for a beat and a first template and selecting a second subset of less than all of the signals based on a comparison between the additional data signals for a beat and a second template that is different from the first template.

The signals included in the first subset are associated with a first type of cardiac activation and the signals included in the second subset are associated with a second type of cardiac activation that is different than the first type of cardiac activation.

Processing the subset of the synchronized signals can include processing the first subset of signals to determine a first set of physiological information at multiple locations of the endocardium surface. The method can also include processing the second subset of signals to determine a second set of physiological information at multiple locations of the endocardium surface.

The method can also include displaying at least a portion of the determined physiological information. The physiological information can be electrical information.

The method can also include the determined physiological information to guide treatment of the heart cavity. The treatment can include ablation of one or more selected regions of the heart. The method can also include repeating the measurement of catheter electrode signals and the determination of the physiological information after the ablation treatment. The treatment can include cell therapy, gene therapy, or the application of other biological agents. The determination of the physiological information at the multiple locations of the endocardium surface further can include applying a transformation function to the signals for the group, wherein the transformation function relates signals measured from at least some of the different positions of the catheter in the heart cavity to the physiological information at the multiple locations of the endocardium surface. The determination of the physiological information at the multiple locations of the endocardium surface further can include determining the transformation function by calculating a forward transformation for relating the physiological information at the multiple locations of the endocardium surface to the signals measured for the different positions of the catheter in the heart cavity and inverting the forward transformation. Inverting can include reformulating an underdetermined matrix inversion by regularization. The inverting can include a least square minimization.

The method can also include aligning the signals relative to a phase in an electrical cycle of the heart. The method can also include generating the template representing an exemplary beat of interest. The method can also include synchronizing the signals by aligning the additional data signal with the templates representing the exemplary beats of interest. Aligning the physiological data signal with the templates representing the exemplary beats of interest can include computing a cross-correlation between the template and the additional data signal. The one or more additional data signals can include multiple physiological data signals.

Computing the criteria based on the comparison of the one or more additional data signals and the corresponding signal template can include, for each of the physiological data signals, aligning the template and the physiological data signal using a cross-correlation calculation to generate a time offset factor. Synchronizing the signals further can include averaging the time offset factors for each of the cross-correlation calculations to determine an average time offset factor. The one or more additional data signals can include multiple ECG signals. The one or more additional data signals can include at least one ECG signal and at least one intercardiac electrogram signal. The one or more additional data signals can include a cardiac pacing signal and at least one physiological data signal.

In some aspects, a method for integrating measurements taken over multiple heart beats is disclosed. The measurements can be aligned so they can be treated as if they were taken simultaneously during a single heartbeat. The measurements can also be graded by different metrics so that only measurements that meet certain criteria are kept and used.

In some aspect, systems and methods disclosed herein use a template mechanism of an exemplary beat of interest in order to align the measurements taken over several beats. A similar template mechanism can also be used in order to compare the beats to the beat of interest and to grade them according to their similarity to it.

It is believed that the systems and methods described herein can provide quick and automatic ways to aggregate data acquired over multiple cardiac cycles while keeping the data synchronized and selecting only data that was acquired during beats that share similar characteristics.

Embodiments of the system may also include devices, software, components, and/or systems to perform any features described above in connection with the methods described herein.

Embodiments of the methods and systems generally disclosed herein can be applied to determining the position of any object within an organ in a patient's body such as the patient's heart, lungs, brain, or liver.

As used herein, the "position" of an object means information about one or more of the 6 degrees of freedom that completely define the location and orientation of a three-dimensional object in a three-dimensional coordinate system. For example, the position of the object can include: three independent values indicative of the coordinates of a point of the object in a Cartesian coordinate system and three independent values indicative of the angles for the orientation of the object about each of the Cartesian axes; or any subset of such values.

As used herein, "heart cavity" means the heart and surrounding tissue.

Unless otherwise defined, all technical and scientific terms used herein have the same meaning as commonly understood by one of ordinary skill in the art to which this invention belongs. In case of conflict with documents incorporated herein by reference, the present document controls.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

Like reference symbols in the various drawings indicate like elements.

DETAILED DESCRIPTION

Figure 1:
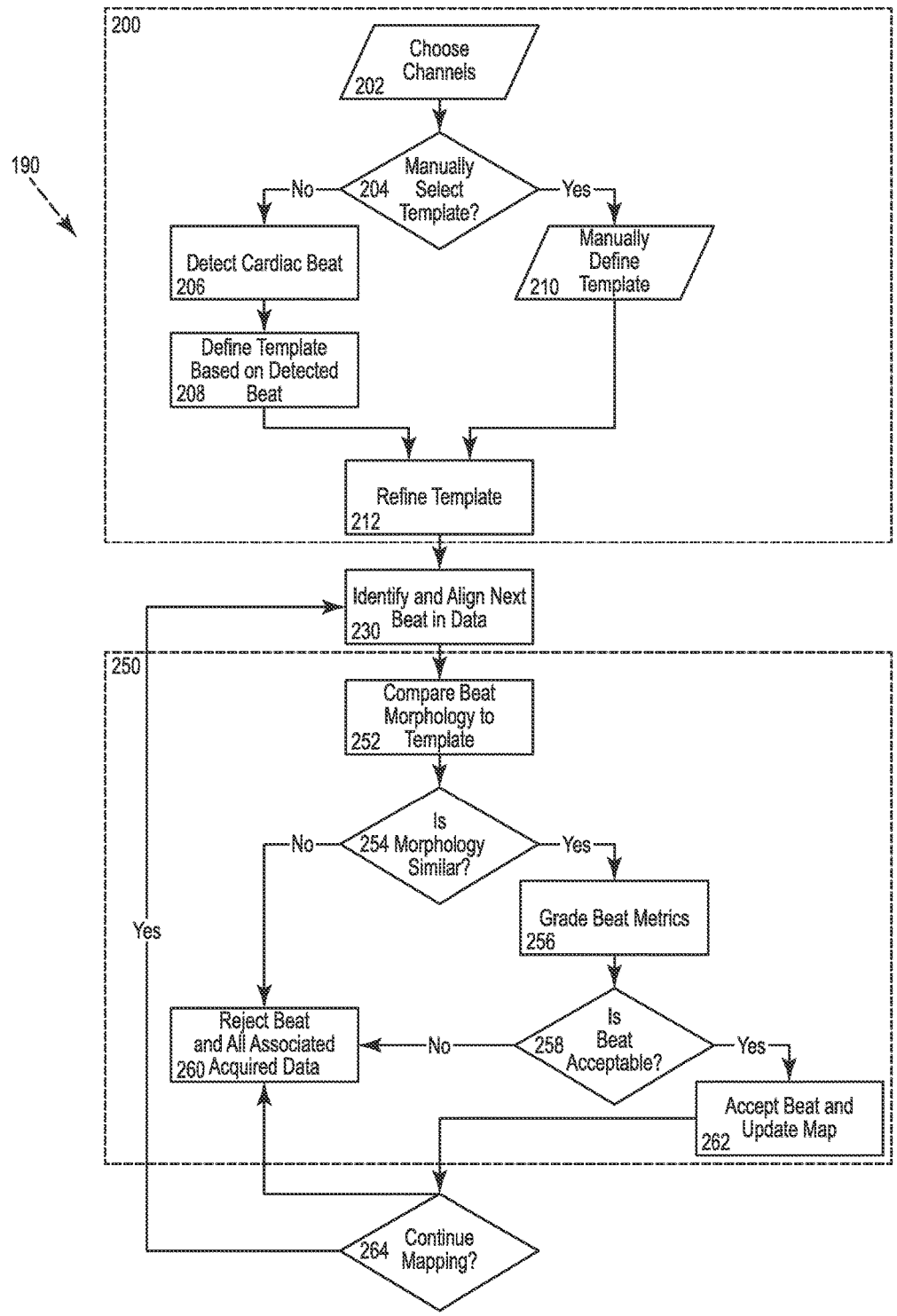
FIG. 1 is a flow chart of a template generation and alignment process.

Systems and methods are disclosed herein that provide a way to quickly and automatically integrate measurements taken over multiple heart beats into a single cardiac map while selecting and keeping only heart beats that share similar characteristics.

In general, cardiac mapping systems can be used for generating different types of maps. Such maps display electrical data, anatomical data, or a combination of both, and aid physicians in determining the source of arrhythmias and in guiding therapeutic treatment, often in the form of RF ablation. An exemplary mapping system is described, for example, in U.S. Pat. No. 7,515,954, entitled "NON-CONTACT CARDIAC MAPPING, INCLUDING MOVING CATHETER AND MULTI-BEAT INTEGRATION" and filed Jun. 13, 2006, the contents of which is incorporated by reference herein in its entirety.

The physiological information displayed to physicians is usually based on signals measured over several heart beats. The signals can be collected at a single catheter location within the heart chamber, but usually are collected in several locations. The ability to perform three-dimensional mapping by integrating multiple measurements taken over multiple separate beats and possibly over multiple catheter locations often introduces synchronization challenges.

When signal acquisition takes place over several heart beats the system synchronizes all the different measurements taken at different times. A synchronization mechanism is used to enable the system to acquire signals at substantially the same cycle of heart's electrical activity. Such synchronization provides way to integrate the measurements to a single set and to treat such measurements as if they were all taken simultaneously. Additionally, in embodiments where signal acquisition is performed in several locations in the heart chamber, the multiple sets of signals are processed to generate a single set of raw data used for the map generation. The same synchronization mechanism can provide a way to consolidate the signals from the catheter's various locations into a composite set. The signals can be treated as though they were obtained at one time from all the positions sampled by the catheter's electrodes for the different positions of the catheter in the heart chamber.

The timing of a time reference point is often used to ensure proper gating for the collection of data during the same phase of each cardiac cycle. In addition, the timing of all electrophysiological information displayed on the completed three-dimensional map is relative to the reference point. A time reference point can be based on a reference point such as a maximum, minimum, or inflection point in a signal.

Historically, in some examples, one reference signal, called the reference electrogram, is selected and used for synchronization. In this method, the reference electrogram is the used as a reference marker that the entire mapping procedure is based on. Any body surface ECG lead or infracardiac lead may serve as a reference electrogram. The reference point of the reference electrogram may be the maximum or minimum value, or maximum or minimum slope.

For example, for the generation of a certain map during sinus rhythm, lead II of the body surface ECG might be chosen as the reference electrogram, with the reference point being the maximum voltage. Such settings will usually provide the peak of the R-wave as the reference point (a reference point based on a distinct feature in the signal, which is a common practice, is often referred to as a fiducial point). Then, all of the activation timing information acquired by the mapping catheter during the mapping will be relative to the surface lead's reference point, with the acquisition being gated so that each point is acquired during the same part of the cardiac electrical cycle.

It may be seen that, in the example above, a prerequisite of the mapping procedure, which is sequential in nature, is that the cardiac rhythm will be monomorphic and stable, and that the reference point determined on the reference channel is reproducible at each sampled beat. The signals can be treated as if they were all taken simultaneously only if they are all measurements of the same activation sequence. In the same manner, signals can be treated as though they were obtained at one time from all the positions sampled by the catheter only if the anatomical structure of the cardiac chamber is consistent across all catheter positions. Mapping may be performed during various cardiac activation sequences such as sinus rhythm, an arrhythmia, or cardiac pacing. However, individual maps can be created for each type of activation sequence to keep the gating, cardiac activation patterns, and anatomical structures as similar as possible in each individual map.

When a map is generated using a single contact electrode, each acquired point is displayed separately on the map. It is possible to select a single point, examine the signals acquired in that point, and correct synchronization problems by manually adjusting the reference point. A mis-aligned acquisition will often be visible on the map, because the effect of such a point is local in nature as each point is affected only by a single beat that was acquired in that position. Such mis-alignments can therefore be located and manually corrected.

However, when a map is generated using multiple electrodes simultaneously, during either a contact or a non-contact mapping procedure, a manual correction may not be possible. The amount of data collected in each cardiac cycle cannot be validated manually in real time. Furthermore, in a non-contact procedure, all the acquired data is blended together through a computational process. The effect of a mis-aligned beat is a degradation of the quality of the entire map, which makes finding such a beat and manually correcting it not practical during a clinical procedure. This makes signal alignment, beat synchronization and selection of beats sharing the same morphologies—much more important for obtaining a high quality map. The systems and methods disclosed herein address that need and propose a system and a method for automatically aligning, synchronizing and selection cardiac beats.

As indicated above, systems and methods are disclosed herein that provide a way to quickly and automatically integrate measurements taken over multiple heart beats into a single cardiac map while selecting and keeping only heart beats that share similar characteristics.

In some embodiments, the alignment of multiple beats is done by correlating multiple electrograms to a reference template of a desired morphology. Any number or electrograms can be used simultaneously (e.g., 1, 2, 3, 5, 10, 12, 15, etc.), and any combination of surface ECG and intracardiac signals can be used. A maximum average correlation across all channels can be used for determination of the best fit between the data and the template. Further, in some examples, a user-selected and configurable threshold value can be used to determine which collected signals to use to generate a map of physiological information and in order to include the signals in the map, the average value of the correlation across the channels must be above a threshold.

Templates can be generated either manually or automatically. For example, templates can be generated manually by a user selecting a time interval on a display. In another example, templates can be generated automatically by using an R-wave detector mechanism. In either case the channels to be used for the reference template need to be chosen.

In some examples, a subset of less than all of the signals collected for multiple different beats are included and used to generate the physiological information. The subset of beats that are used can be automatically selected based on correlation between the beat and a template or based on other information related to the beat. For example, each identified beat is scored based on several metrics that can be calculated (e.g., as described in more detail below). Some metrics are related to the beat detection and alignment mechanism. For example, a threshold can be set for a minimum correlation level for keeping a beat (e.g., for using the signals collected during the beat ingeneration of the physiological information). This metric can be used for rejecting beats of different morphologies. Another example is the time interval between consecutive identified beats, which can be compared with the duration of the beat template, and can be used for rejection of ectopic beats. Other metrics that can be used for beat selection can be based on other parameters of the mapping procedure that are important for the validity and the accuracy of the generated map such as the velocity of the mapping catheter or the respiration phase.

These metrics are used for further filtering of the beats, rejecting all beats that do not meet the required criteria and thus would decrease the accuracy and the consistency of the generated map. Selection or rejection of a beat determines whether or not data acquired during this beat is used for mapping purposes. The decision is made automatically for any number of electrodes and any number of catheters that record electoanatomical data during the procedure. A mapping procedure can rely on a single linear mapping catheter, a single multi-electrode contact catheter, a single multi-electrode non-contact catheter, or any combination of the above. This method allows for quick rejection of multiple mapping points without the need for individually checking each point.

FIG. 1 shows an exemplary process 190 that includes a template generation process 200, a beat identification and alignment process 230, and a beat selection process 250. The template generation process 200 includes choosing one or more channels for which electrogram information is collected which will be used for the alignment and beat selection processes (202). The process also includes determining whether the template will be manually selected (204). If the user desires to manually select the template, the user enters information to manually define the template (210). For example, the user can select a time interval on a display and use the beat during the selected time interval as an exemplary beat of interest to define the template. On the other hand, if the user does not desire to manually generate the template, the system can automatically detect the location of a cardiac beat (140) and define a template based on the detected beat (208). Regardless of whether the template beat was selected manually or automatically, the template can optionally be refined by the system (212). Such a refinement process can include, for example, averaging templates for multiple beats to reduce noise that could potentially appear in one of the signals.

After a template of the beat of interest has been defined (note the template can include exemplary signals for each of the channels for which data is collected), the system identifies and aligns collected beat data to the template (230). Various processes can be used to align the beat data to the templates and are described in more detail below.

Once the data collected for a beat has been aligned with the template, the system compares the beat morphology of the information collected to the beat to a template (252) and determines if the morphology is similar (254). If the morphology is not similar enough to the template morphology, the system rejects the beat and all associated acquired data (260). When the beat is rejected, the acquired data for the beat is not used in the generation of physiological information such as voltage or current maps. If the morphology of the beat is similar to the template, the system calculates beat metrics and grades the beat metrics (256). Beat metrics can be calculations or other comparisons used to determine the similarity between the template beat and the measured beat. Based on the results of the beat metrics, the system determines if the beat is acceptable (258). If the beat is not acceptable, the system rejects the beat and all associated acquired data (260). As above, when the beat is rejected, the acquired data for the beat is not used in the generation of physiological information such as voltage or current maps. On the other hand, if the beat is acceptable the system accepts the beat and updates the map or updates the information that will be used subsequently to generate the map (262). The system then determines whether to exit of continue the mapping process 264.

Template Generation

During cardiac mapping procedures many different signals are collected and displayed to the operating physician. Exemplary signals include electrical signals collected by intracardiac catheters and surface ECG leads. The signals are often displayed in real time on a screen which can be viewed by the operating physician. Different cardiac activation sequences generate different signal morphologies. Thus, the signal traces on the screen correspond to the cardiac activation sequences and allow the physician to determine the type of rhythm the patient is experiencing, e.g., based on the signal morphology.

In some cases, the same type of cardiac arrhythmia can take multiple forms, each one resulting in a different morphology. For example, a patient with Ventricular Tachycardia (VT) can suffer from different types of VT, originating from different parts of the ventricle. These different morphologies can look different on the ECG and intracardiac traces, and may even result in different heart rates, despite the fact that all are categorized under the same type of arrhythmia (VT in this case). Often, different morphologies originate from different places in the heart and require separate treatment. For that reason it is important for the physician to differentiate between the different morphologies and to generate a separate electroanatomical map for each of the different morphologies.

Referring back to FIG. 1, in order to separately generate electroanatomical maps for each of the different morphologies, the system can define templates representing each of the different morphologies. More particularly, in order to determine the morphology of interest, a template beat is defined and is later used to identify similar events in the acquired signals. In some examples, the user can manually define the template (210). For example, the user can manually create a template by selecting a time period using a caliper-like tool on the screen. The template interval should include, as a minimum, the interesting part of the morphology of interest, such as the R-wave in the case of ventricular mapping or the P-wave in the case of atrial mapping. In some examples, it can be preferable that the template will be as wide (e.g., cover the same length of time) as a complete cardiac cycle, allowing the alignment and selection process to account for differences in signal throughout the entire duration of the cycle. The user can specify the exact location of a reference point within the selected template, choosing any feature of interest as the baseline for mapping. The reference point is sometimes referred to as the beat marker, or the fiducial point, and is often used as a time reference for relative time measurements during a mapping procedure.

In some examples, the user can further select the channels that are used for the alignment and selection process (202). Any number of channels and any combination of surface ECG and intracardiac channels can be used. In some embodiments, it is believed to be beneficial to use all 12 ECG leads and 2 bipolar measurements of a Coronary Sinus catheter. In other embodiments, less than all of the ECG leads may be used for the alignment and selection process.

Once selected, a template can be refined by averaging of N beats (e.g., N=5, N=10, N=20) that were selected by the same alignment and selection process used for the mapping (212). This refinement process can improve signal to noise ratio of the electrograms and emphasize small features in the signal that can be used for differentiating one morphology from another.

In an alternative embodiment, templates can be generated automatically. For this purpose, a beat detector is used to automatically identify cardiac events (206). Any known method for detecting cardiac beats in ECG or intracardiac signals can be used. One option can be an R-wave detector on one of the ECG leads (e.g. lead II).

Another option is to use an intracardial catheter signal, such as a Coronary Sinus bipolar signal, and to apply a beat detection mechanism similar to that used in implantable cardioverter defibrillator (ICD). A beat template containing the identified beat is then automatically defined (208), having either a width that equals the detected beat duration or a fixed width that can be configured. Any number of channels can be used for the automatically selected template, in the same manner as they are used for the manually selected one (e.g., as described above). Once a preliminary template is selected the same refining method can be used for improving the template (212).

Beat Alignment

Referring again to FIG. 1, in order to process data acquired over multiple beats it is necessary to align the data relative to a specific phase in the electrical cycle (230).

Several methods for aligning of cardiac signals are used for applications such as cardiac gating of imaging systems or high resolution ECG analysis. In these methods, a reference point detector (sometimes called a fiducial point detector) detects the time markers at which particular event occur. For example, it may detect the R wave in surface ECG or activation time of an intracardiac electrogram. See, for example, Jane Raimon, "Alignment methods for averaging of high resolution cardiac signals", IEEE Transactions in Biomedical Engineering, Vol. 38 No. 6 (June 1991); Brooks, Dana, "Improved alignment method for noisy high-resolution ECG and Holter records using multiscale cross-correlation", IEEE Transactions in Biomedical Engineering, Vol. 50, No. 3 (March 2003); Breithardt, Gunter, "Standards for analysis of ventricular late potentials using high-resolution or signal-averaged electrocardiography", Circulation, Vol. 83, No 4 (April 1991).

In some examples, a correlation function such as a cross-correlation can be used to align a signal with a template. The correlation function results in the determination of a time offset or time lag that provides the time offset for the closest match of the measured signals to the template. An exemplary cross-correlation function is shown below in equation 1. The template, y, having n sample, is cross-correlated with the data signal, x, that needs to be synchronized. The time lag, m, which results in the highest correlation, is defined as the required time offset between the signals for alignment purposes.

$$C_m = \frac{\sum_{i=0}^{n-1} x_{i+m} \cdot y_i}{\sqrt{\sum_{i=m}^{n+m-1} x_i^2} \sqrt{\sum_{i=1}^{n} y_i^2}} \quad (1)$$

Figure 2:
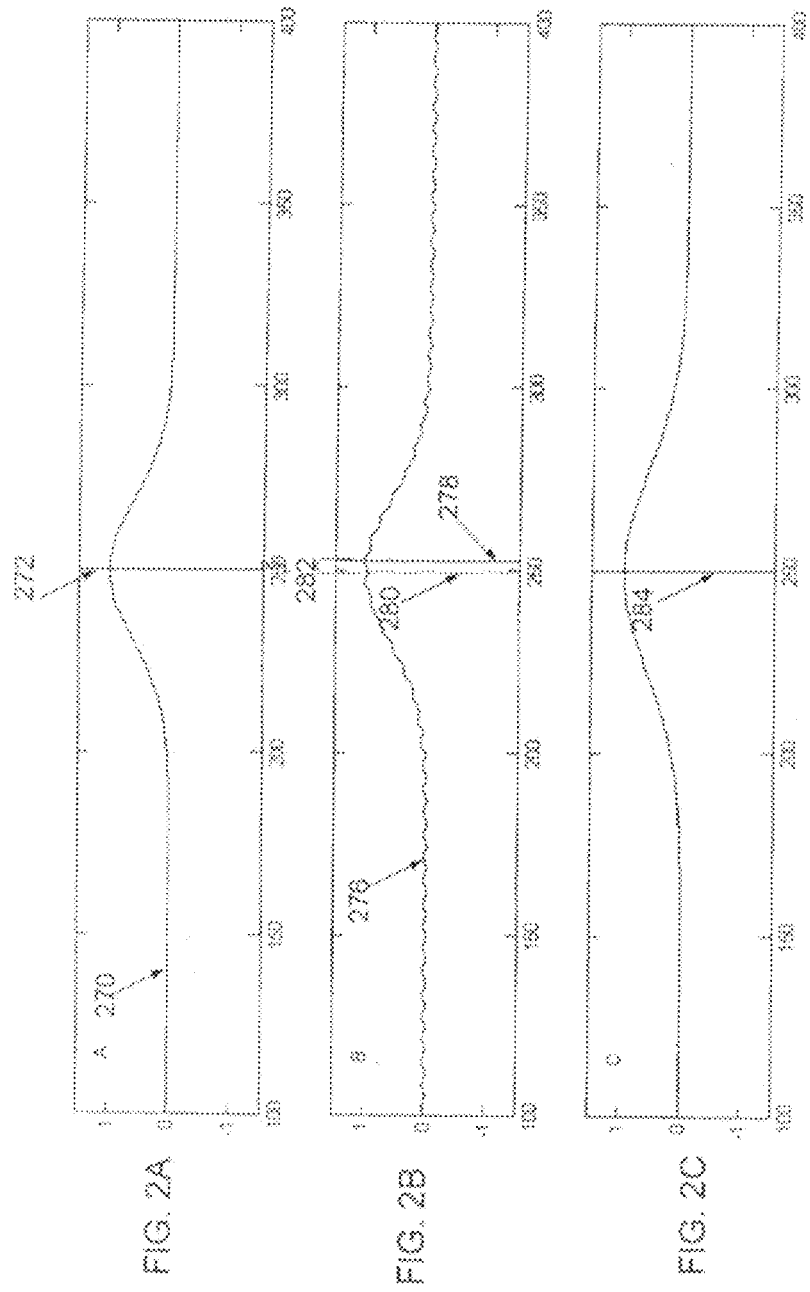
FIG. 2A shows an exemplary template.
FIG. 2B shows an exemplary data signal.
FIG. 2C shows an exemplary aligned data signal.

FIGS. 2A-2C show an example of synchronization using cross-correlation. FIG. 2A shows a template 270 of an exemplary beat of interest. The template includes a defined beat marker 272. In this example, the beat marker 272 is located at the inflection point (e.g., the peak) of the template 270. FIG. 2B shows a noisy signal 276 aligned with the template signal 270. A fiducial point 278 is detected at the peak of the signal. It can be seen that the peak of the signal 278 has an offset 282 from the time location of the actual beat marker 280 from the template signal. FIG. 2C shows the cross-correlation between the template 270 and the noisy signal 276, and the peak of the correlation 284 is used as the reference point. It can be seen that the peak of the correlation 284 is synchronized with the original beat marker of the template 272.

It is believed that the use of multiple electrogram signals for synchronization can improve the accuracy of the alignment mechanism. A cross-correlation value is computed for each channel, and the reference points are defined when the average cross-correlation between all of the template and synchronization signals reach a maximum.

Since all signal channels are synchronized in time only a single offset value is required for aligning all the channels of a certain beat to the reference template. The reference points detector outputs the time markers $P_1 \ldots P_B$ at which the reference points are detected. These time markers are then used to align the acquired signals.

Similar to template creation, any number of signal channels can be used for synchronization purposes. It is assumed that the channels that are chosen for synchronization purposes are consistent over time and that they record the same signal as long as the cardiac activation sequence is not changing. For that reason it is important to use signals that are collected from a stationary position in the heart, and not signals that are collected by roving catheters. It should be noted that changing the location of ECG patches or intracardiac catheters changes the morphology of the signal acquired on that channel, resulting in a degradation of correlation values. This could interfere with the synchronization results. In a similar way, signal manipulations, such as any filter applied to the signals, should remain constant between the time of template generation and the alignment process.

In some examples, cardiac pacing is used during a mapping procedure. In cardiac pacing, a stimulus signal is applied to the heart using a catheter and paces the heart at a defined rate from a defined location. This pacing takes over the natural pace and the natural activation sequence of the heart. In this scenario the synchronization signal may come from the pacing apparatus. It is possible to replace the cross-correlation mechanism when pacing is performed and to pass the time markers associated with the synchronization signal as reference points. It is important to note that in this case beats can be aligned and aggregated based on the pacing signal alone, regardless of whether the pacing was captured by the cardiac chamber or whether the pacing lead moved within the heart and the paced morphology changed.

In some additional examples, to improve the accuracy of the alignment from the situation of aligning based on the pacing signal alone, the pacing signal is used as one of the channels of the template in addition to ECG and intracardiac signals. Cross-correlation can be computed on this channel for alignment purposes while also being computed for channels associated with cardiac activation. This method differentiates between different paced morphologies and can detect instances of pacing signal that was not captured by the cardiac chamber. It is believed that the clean and strong pacing signal can improve the cross-correlation based alignment when compared to using only ECG and intracardiac signals, and is believed to provide an advantage to the alignment mechanism during cardiac pacing.

Beat Selection

Once different beats are identified and are aligned to allow synchronization of the different beats in time, in some embodiments, it is preferable to determine which beats should be used for generating a cardiac map. Data, such as electrical data from one or more catheters and location data of these catheters or their electrodes, is usually collected during the time period of each identified beat. As mentioned before, it is preferable to only aggregate information that was acquired during cardiac beats sharing similar characteristics in order to generate coherent physiological data such as a coherent map.

Systems and methods disclosed herein can automatically and efficiently select a subset of the identified beats that share similar characteristics in order to quickly generate an electroanatomical map of the event of interest (e.g., as shown in portion 250 of FIG. 1).

The selection mechanism is based on grading metrics that are applied to the identified beats. Each metric provides a grade for each beat. The grade provides a variable associated with the similarity between the beat and a beat of interest. Some of the metrics are continuous, meaning the grade is a continuous variable, and a threshold, that possibly can be user configurable, is used in order to determine whether a beat is accepted and selected. Other metrics are binary, determining a pass or fail grade for each beat.

Any number and any combination of metrics can be used for automatically selecting the beats that will be aggregated for mapping purposes.

One metric believed to be useful for beat selection is a metric that provides a correlation grade between the identified beat and a template of interest (252). This metric is calculated as described in Equation 1 (above) and, in some embodiments, it is calculated as a part of the alignment process. The maximum average correlation that was found when the beat was identified is compared to a threshold level, T, to determine how similar the identified beat is to the saved template. Exemplary threshold levels can be greater than about 0.7 (e.g., T=0.7, T=0.75, T=0.8, T=0.85, T=0.9, T=0.95). It is believed that a preferred value for the threshold is T=0.9. Based on the comparison of the computed correlation grade to the threshold, the system determines if the beat morphology is similar (254).

A different threshold can be used for alignment purposes than the one used here for beat selection purposes, so it is possible to identify a beat and to align it to the template but still reject the beat based on the grading metric. It is also important to remember that this is an average correlation value over a multiple number of signal channels, which may include both surface ECG and intracardiac electrograms.

A high correlation between the signals acquired during the beat under investigation and the template indicates that the beat is of similar morphology and that the cardiac activation sequence is consistent between the two time periods. This indicates that the beats are similar enough and can be aggregated to generate a single map while assuming that information that was acquired in different times and in different locations still represents the same biological and clinical phenomena.

In some additional embodiments, a modified method can be used. In such embodiments, a configurable number of channels, M, (e.g., M=2 channels, M=1 channel, M=3 channels) are dropped before the correlation metric is computed (e.g., the channels are not used to determine whether to keep the beat). Dropping one or more channels prior to computation of the correlation metric can be advantageous when some channels experience noise or interference that reduces the correlation between the signal and the template on these channels. Thus, instead of lowering the correlation threshold for acceptance for all the channels, some tolerance is added by dropping the worst M channels before computing the average correlation.

Figure 3:
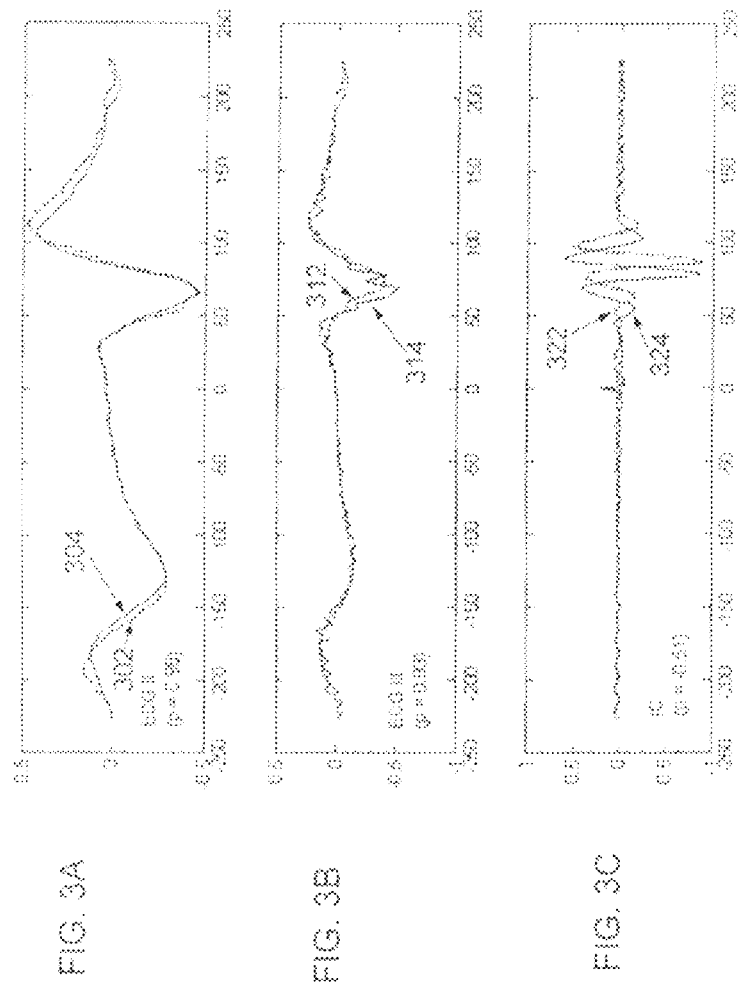
FIGS. 3A-3C show exemplary data signals and templates.

FIGS. 3A-3C show multiple channels and signals collected on the multiple channels and demonstrates the importance of using multiple channels for synchronization and selection purposes. FIGS. 3A-3C show three traces taken simultaneously on three different channels. Two of the channels are surface ECG leads (e.g., the channels shown in FIGS. 3A and 3B), and one is an intracardiac signal taken from a stationary catheter (e.g., the channel shown in FIG. 3C). The solid lines (lines 304, 314, and 324) are the template signals of the beat of interest, while the dashed lines (lines 302, 312, and 322) are the live or measured signals. As seen in the FIGS. 3A and 3B, according to the surface ECG leads there is a good match between the template and the live traces (e.g., between template 304 and signal 302 and between template 314 and signal 312). However, according to the third signal (FIG. 3C) it can be determined that the beat needs to be rejected because there is not a good match between the template 324 and the live or measured signal 322.

In case the morphology of the beat is not close enough to the morphology of the template, the beat is being rejected and the data collected is not used for electroanatomical mapping (260). Otherwise, the beat is being investigated further.

Additional Metrics for Beat Selection

Additional metrics that can be used for the automatic selection mechanism are described below.

Beat duration—The system can automatically reject identified beats that occur too close to one another in the time domain. The duration of the template can be used as a measure for the expected beat duration, T, and a minimum (e.g., 0.7T, 0.75T, 0.8T, 0.85T) can be allowed for a beat duration if the beat is to be used in generation of the physiological information. If more than one beat is identified within a time period that is smaller than the allowed duration—only the one with the higher correlation is accepted. This mechanism is believed to be advantageous in rejecting of ectopic beats that can either be generated naturally in a diseased heart or be induced by catheter movement in the heart during a clinical procedure.

Figure 4:
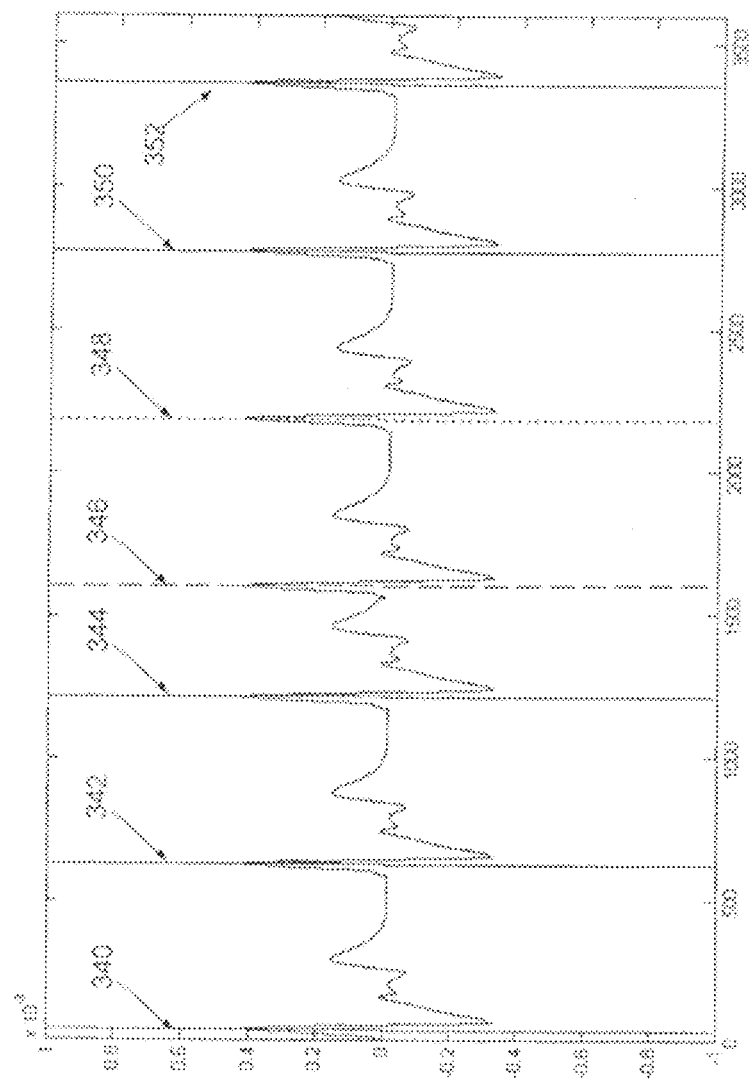
FIG. 4 shows an exemplary beat train.

FIG. 4 shows an exemplary ECG trace used for rejection of beats based on beat duration. A sequence of cardiac beats that are recorded from a surface ECG lead is displayed. The vertical lines (e.g., lines 340, 342, 344, 346, 348, 350, and 352) represent reference points that were identified by the synchronization mechanism. The first dashed line (e.g., line 346) shows a beat that has a similar morphology to the template, but is too short (e.g., the duration of the beat is shorter than a threshold duration). This beat is rejected according to the beat duration criterion.

Signal energy—The system can further take into account the amplitude of the signals and compare the energy of the beat under investigation to the energy of the template beat. Since correlation calculations normalize the signals, a change in signal amplitude cannot be detected by a correlation based metric. It is believed that adding another metric comparing the amplitudes can improve the results. An exemplary equation for generating an energy metric, E, that compares the energy of the beat under investigation to the energy of the template beat, is shown in Equation 2.

$$E = \max\left(\frac{\sqrt{\sum_{i=1}^{n} x_i^2}}{\sqrt{\sum_{i=1}^{n} y_i^2}}, \frac{\sqrt{\sum_{i=1}^{n} y_i^2}}{\sqrt{\sum_{i=1}^{n} x_i^2}}\right) - 1 \quad (2)$$

Where E is the energy metric for a single channel, y is the template of that channel, and x is the corresponding section of the acquired signal of that channel after the signal was aligned to the template. Similar to the correlation metric, an average of all channels can be computed for determining the metric for the beat, and a number of channels can be dropped to avoid biases resulting from noisy channels.

First beat in train—It is believed that when the cardiac activation is changed to a new morphology the first beat of the new morphology is a transition beat and that activation sequences and mechanical contraction of the heart are different than those of the following heart beats. For that reason, in some embodiments, it can be advantageous to reject the first beat in a new beat train of a morphology of interest. This can be identified by measuring the time duration between the current beat under investigation and the previous beat that shared the same morphology. If the time interval is too large (e.g., more than 1.3T-1.7T such as 1.5T, T being the duration of the template) the beat can be assumed to be the first in a new train.

Referring back to FIG. 4, in the beat train shown, the short beat (identified by line 346) is followed by the rhythm returning to normal. However, the first beat after the rejected beat (e.g., as indicated by line 348). This is an example of a first beat in a train that is rejected based on the explained criterion.

Respiration phase—Respiration motion is believed to be major source of inaccuracy in electroanatomical mapping procedures. The anatomy of the heart is different in different phases of the respiratory cycle, as the heart moves inside the chest cavity along with the changing volume of the lungs. Different methods can be used in order to determine the phase of the respiratory cycle. A chest belt can be installed on the patient and provide a signal that corresponds to the volume of the chest thus providing the respiratory phase. Another option is to apply a low-pass filter to the location indication of a catheter in the heart (e.g. a catheter in the Coronary Sinus). Such a filter, if tuned appropriately (e.g., having a cut-off frequency of 0.2 Hz) will reject the high frequency content that is caused by the cardiac contraction, leaving a clean signal corresponding to the motion of the heart caused by respiration. The respiration signal can be used as a grading metric, assigning a value to each identified beat based on the value of the respiration signal at the time of the beat. Appropriate thresholds can be configured to accept only beats that share the same respiratory cycle.

Figure 5:
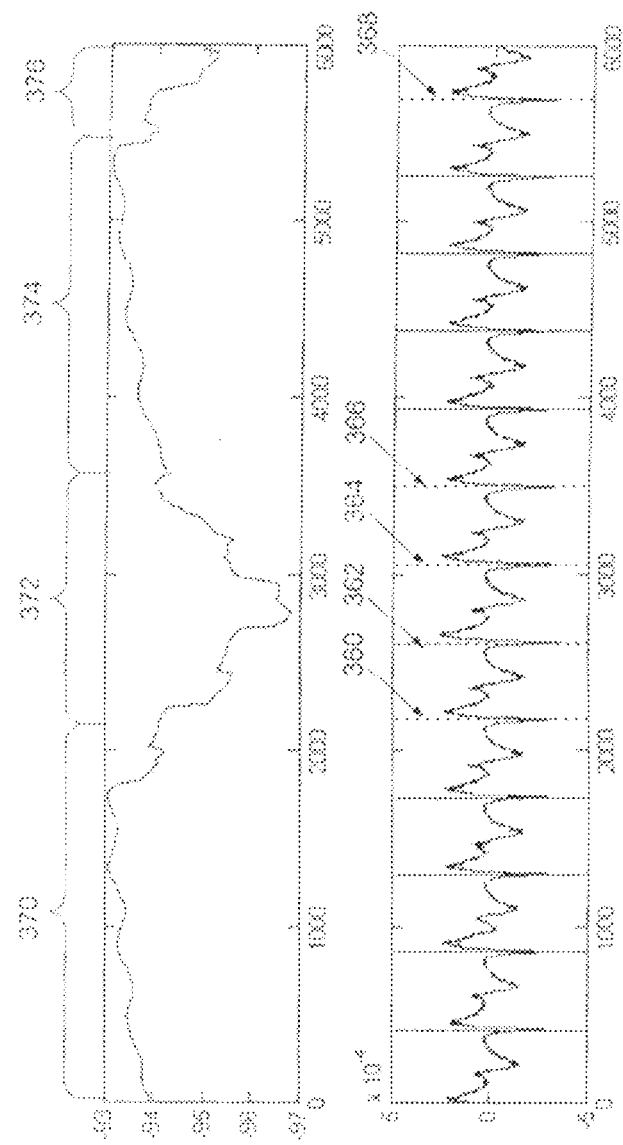
FIG. 5A shows an exemplary representation of a respiration phase.
FIG. 5B shows a graph of a data signal aligned to the respiration phase of FIG. 5A.

FIGS. 5A and 5B show an example of signals used to determine and identify beats sharing the same respiratory cycle. FIGS. 5A and 5B show two traces acquired simultaneously. The trace in FIG. 5A shows a measure of the respiration state. The trace in FIG. 5B shows a signal collected from a surface ECG lead. Vertical lines over the bottom trace represent reference points determined by the beat synchronization mechanism. The dashed lines (e.g., lines 360, 362, 364, 366, and 368) are beats that were rejected due to the respiration motion detected in the top trace. For example, beats collected during the non-stable portions of the respiration cycle (e.g., portions 372 and 376) are rejected and only beats that were collected in the stable state of the respiratory cycle (e.g., portions 370 and 374) are kept and used for mapping.

Cardiac contraction—A change in the mechanical structure of a cardiac chamber can be detected, for example, by using a conductance catheter, using measurement of the electrical conductance of the blood contained in the cavity. For this purpose, a catheter containing current injecting electrodes and potential measuring electrode is used for generating an intracavitary electric field and measuring the resulting voltage gradients. The measured conductance, affected by the volume of the chamber, is a proxy for measuring the mechanical contraction. The chamber volume can be measured during each cardiac beat and a metric can be formed by comparing the measured value to a threshold. Furthermore, a continuous measurement of the volume can be obtained and used as a signal trace. The signal can be collected while the template is defined, and again while the mapping data is acquired. The same correlation method mentioned above can be applied to this signal, enabling differentiation between beats that share similar electrical morphologies but differ in the mechanical cardiac contraction sequence.

Many more metrics can be designed and computed for determining the consistency and quality of beats. It should be appreciated that any combination of metrics can be used, and that different combination can be useful for different clinical needs. Furthermore, different configurations and different thresholds can be applied for different needs and the invention is not limited to a specific embodiment. All numbers and calculations are given as examples only and should not be considered as limitations of the proposed system.

Referring back to FIG. 1, in the mapping process, all desired metrics are calculated (256) and based on the grades a decision is being made for the identified beat (258). In case the beat is rejected based on its different grades the data collected is not used for electroanatomical mapping (260). In case the beat is accepted, the collected data is accepted as well and used for updating the generated electroanatomical map (262). In either case, of the mapping procedure is to proceed (264), the process is repeated for the next beat that is identified in the collected data.

In some cases, within an accepted beat, when multiple electrodes were collecting electrical data, it is desired to further select a subset of the signals. For example, when collecting non-contact signals using an electrode array, it is possible that some electrodes touch the cardiac wall and the motions artifacts that are added to the signals of these electrodes make them unusable. An additional functionality in the selection process is the ability to select, within an accepted beat, a subset of the signals collected during that beat, and use only that subset for mapping purposes. A possible mechanism for such selection process can be to cross-correlate the signals from all electrodes that collected data during the beat, and reject signals that are very different than their neighbors.

Figure 6:
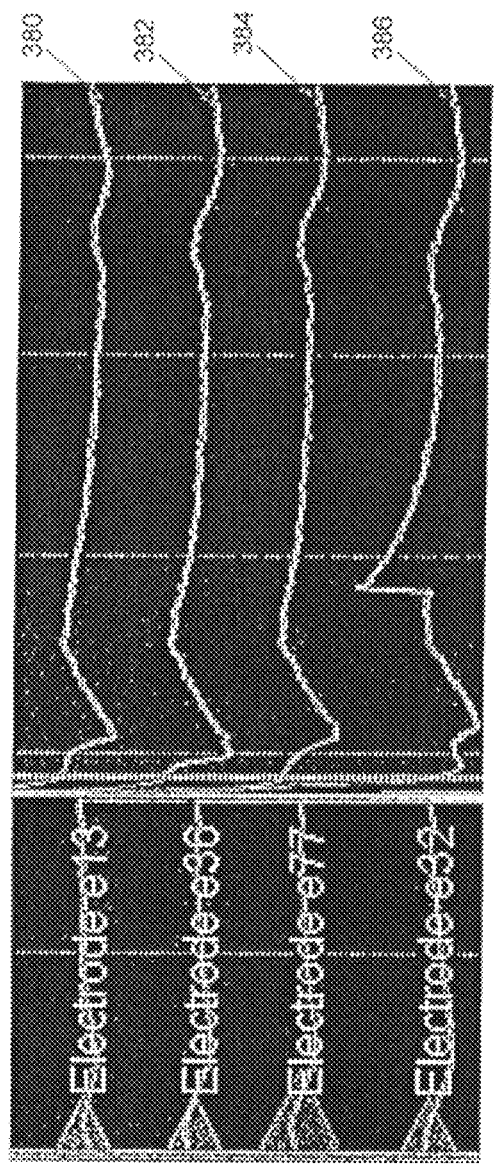
FIG. 6 shows a graph of signals collected from multiple electrodes.

FIG. 6 shows signals that were collected simultaneously from 4 electrodes. The top 3 signals 380, 382 and 384 share similar characteristics, while the bottom signal 386 is very different and has a noticeable step response. This signal can be rejected based on cross-correlation values between all measurements.

Beat Classification

Figure 7:
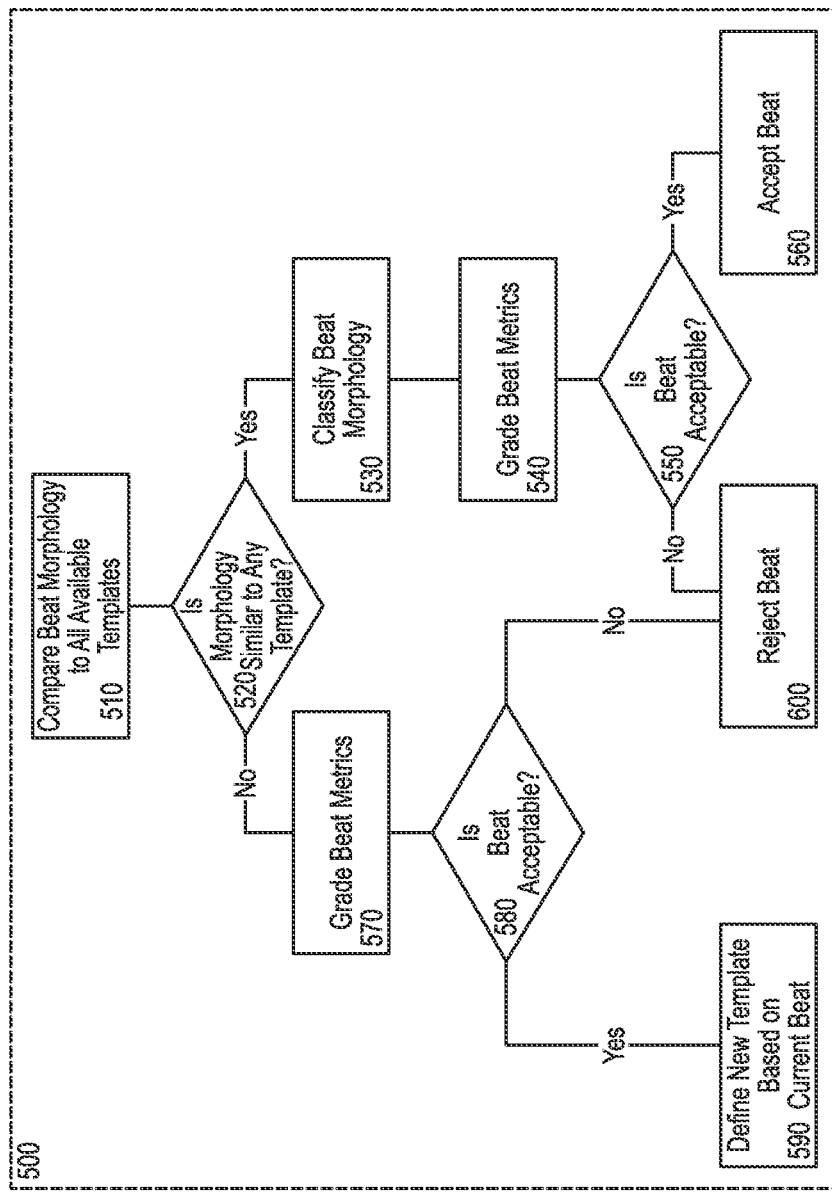
FIG. 7 is a flow chart of a beat selection process.

In some additional embodiments, multiple templates of different beat morphologies can be defined (each template can include multiple exemplary signals for each of the channels for which data is collected). In such a case data is compared to all templates and beats will be grouped according to the different morphologies. This allows for classification of different beats and for the easy and quick generation of maps of different morphologies. FIG. 7 shows an exemplary process for grouping of beats according to their morphologies. The process shown in FIG. 7 can replace block 300 in FIG. 1.

The identified beat is compared in the same manner described above to each one of the available templates (510). The same threshold criterion and the same mechanism for dropping M number of signals describe above can be used as well.

If there is a fit between the identified beat and any of the available templates (520), the beat is classified as one that belongs to that template (530), and then the rest of the beat metrics are computed for the beat (540). Once again, any number and any combination of metrics can be used, according to the clinical scenario. Based on the grades a decision is being made for the identified beat (550). In case the beat is rejected based on its different grades the data collected is not used for electroanatomical mapping (600). In case the beat is accepted, the collected data is accepted as well and used for updating the generated electroanatomical map that corresponds to the template that matched the identified beat (560).

When an automatic template generation mechanism is used, the functionality can be further expanded to automatically generate several different templates for different morphologies and to automatically classify the different beats. In one possible embodiment the beat detector mentioned earlier is used to automatically identify cardiac beats. When a new beat detected but the selection process does not recognize the beat as one that fits any of the available templates (520) it can be assumed that a new morphology is encountered. The rest of the beat metrics are then computed for the beat (570). Once again, any number and any combination of metrics can be used, according to the clinical scenario. Based on the grades a decision is being made for the identified beat (580). In case the beat is rejected based on its different grades the data collected is not used for electroanatomical mapping, and no new template is created (600). In case the beat is accepted, a new template is defined based on the beat (590). The collected data is accepted as well and is used for generating the beginning of a new electroanatomical map that corresponds to the new identified morphology.

In this scenario, a new template can be generated and by that a new class of beats is defined. Such a mechanism can assist in tracking and mapping of transient events and in collection of data for multiple morphologies in parallel.

Representative System

Figure 8:
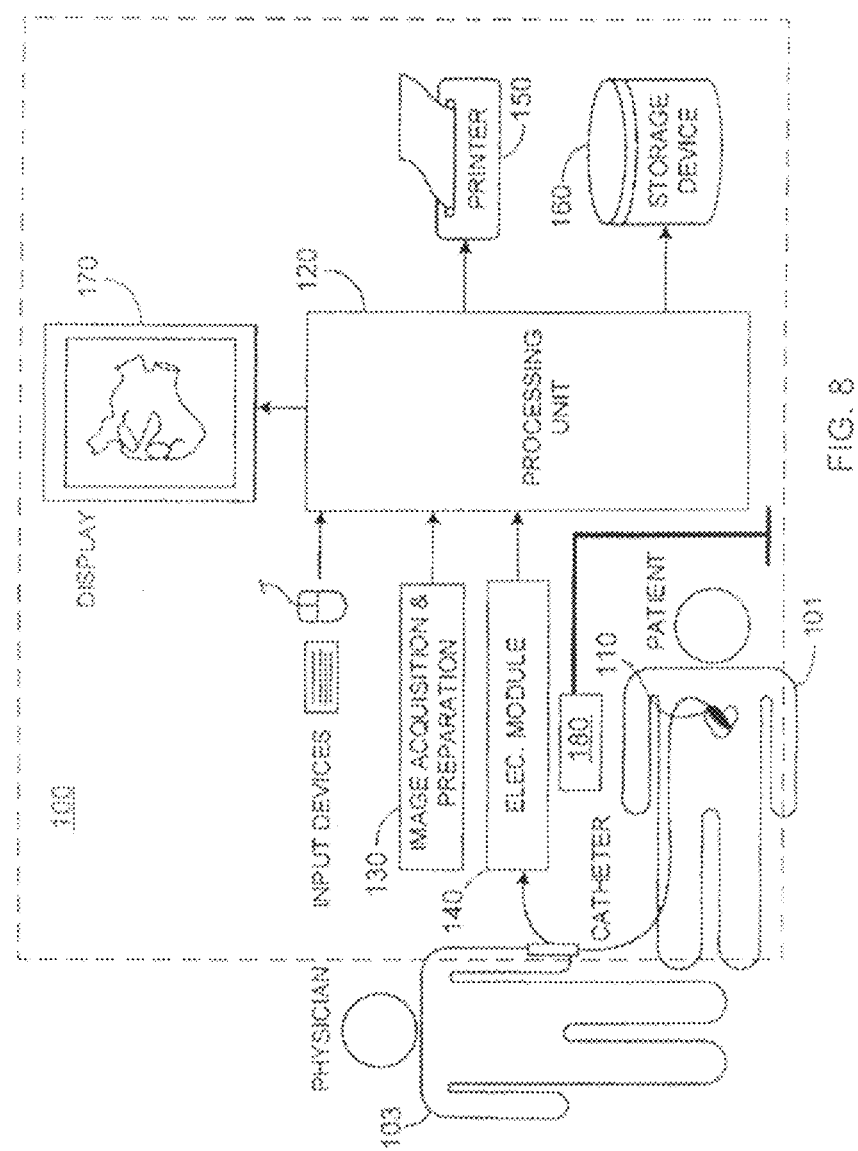
FIG. 8 is a schematic diagram of an exemplary system.

FIG. 8 shows a schematic diagram of an exemplary embodiment of a non-contact system 100. The non-contact system 100 includes a moveable catheter 110 having multiple spatially distributed electrodes. During the signal acquisition stage of the non-contact mapping procedure the catheter 110 is displaced to multiple locations within the heart chamber into which catheter 110 is inserted.

In some embodiments the distal end of the catheter 110 is fitted with multiple electrodes spread somewhat uniformly over the catheter. For example, the electrodes may be mounted on the catheter 110 following a 3D olive shape. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, or shape memory material such as Nitinol.

At each of the locations to which the catheter 110 is moved, the catheter's multiple electrodes acquire signals resulting from the electrical activity in the heart cavity. Consequently, reconstructing and presenting to a user (such as a doctor and/or technician) physiological data pertaining to the heart's electrical activity may be based on information acquired at multiple locations, thereby providing a more accurate and faithful reconstruction of physiological behavior of the endocardium surface. The acquisition of signals at multiple catheter locations in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments the catheter 110 is moved to more than three locations (for example, more than 5, 10, or even 50 locations) within the heart chamber. Further, the spatial range over which the catheter is moved may be larger than one third ($\frac{1}{3}$) of the diameter of the heart cavity (for example, larger than 35%, 40%, 50% or even 60% of the diameter of the heart cavity). Additionally, in some embodiments the reconstructed physiological information is computed based on signals measured over several heart beats, either at a single catheter location within the heart chamber or over several locations. In circumstances where the reconstructed physiological information is based on multiple measurements over several heart beats, the measurements are synchronized with one another so that the measurement are performed at approximately the same phase of the heart cycle. The signal measurements over multiple beats can be synchronized based on features detected from physiological data such as surface ECG or intracardiac electrograms.

Non-contact mapping system 100 further includes the processing unit 120 which performs several of the operations pertaining to the non-contact mapping procedure, including the reconstruction procedure to determine the physiological information at the endocardium surface (e.g., as described above). To expedite the computational operations performed by the non-contact mapping system 100, the processing unit 120 can compute, generally prior to the insertion of the catheter into the heart chamber and/or before signal acquisition by the catheter's electrodes has commenced, transformation functions that can be used in real-time to facilitate the reconstruction process. Once the catheter 110 is inserted and is displaced to a particular location in the heart chamber, the mapping procedure can be performed expeditiously by computing in real-time those transformation components that were not computed ahead of the signal acquisition stage, and combining those components with the appropriate pre-processed transformation components to obtain the overall transformation function(s). That overall transformation function is applied to the acquired raw data to perform the inverse reconstruction operation.

The processing unit 120 also performs a catheter registration procedure. The location of the catheter 110 inserted into the heart chamber can be determined using a conventional sensing and tracking system (not shown) that provide the 3D spatial coordinates of the catheter and/or its multiple electrodes with respect to the catheter's coordinate system as established by the sensing and tracking system. However, to perform the mapping procedure and reconstruct physiological information on the endocardium surface, it is necessary to align the coordinate system of the catheter 110 with the endocardium surface's coordinate system. The processing unit 120 (or some other processing module of system 100) determines a coordinate system transformation function that transforms the 3D spatial coordinates of the catheter's locations into coordinates expressed in terms of the endocardium surface's coordinate system, or vice-versa.

The processing unit 120 also performs post-processing operations on the reconstructed physiological information to extract and display useful features of the information to the operator of the system 100 and/or other persons (e.g., a physician).

As further shown in FIG. 8, the signals acquired by the multiple electrodes of catheter 110 are passed to the processing unit 120 via the signal conditioning module 140. The signal conditioning module 140 receives the signals communicated from the catheter 110 and performs signal enhancement operations on the signals before they are forwarded to the processing unit 120. Signal conditioning hardware is used to amplify, filter and continuously sample intracardiac potential measured by each electrode. The intracardiac signals typically have a maximum amplitude of 60 mV, with a mean of a few millivolts. In some embodiments the signals are bandpass filtered in a frequency range (e.g., 0.5-500 Hz) and sampled with analog to digital converters (e.g., with 15-bit resolution at 1 kHz). To avoid interference with electrical equipment in the room, the signal can be filtered to remove the frequency corresponding to the power supply (e.g., 60 Hz). Other types of signal processing operations such as spectral equalization, automatic gain control, etc. may also take place. The resultant processed signals are forwarded by the module 140 to the processing unit 120 for further processing.

As further shown in FIG. 8, the non-contact mapping system 100 also includes peripheral devices such as printer 150 and/or display device 170, both of which are interconnected to the processing unit 120. Additionally, the mapping system 100 includes storage device 160 that is used to store data acquired by the various interconnected modules, including the volumetric images, raw data measured by electrodes and the resultant endocardium representation computed there from, the partially computed transformations used to expedite the mapping procedures, the reconstructed physiological information corresponding to the endocardium surface, etc.

Other Embodiments

The methods and systems described herein are not limited to a particular hardware or software configuration, and may find applicability in many computing or processing environments. The methods and systems can be implemented in hardware, or a combination of hardware and software, and/or can be implemented from commercially available modules applications and devices. Where the implementation of the systems and methods described herein is at least partly based on use of microprocessors, the methods and systems can be implemented in one or more computer programs, where a computer program can be understood to include one or more processor executable instructions. The computer program(s) can execute on one or more programmable processors, and can be stored on one or more storage medium readable by the processor (including volatile and non-volatile memory and/or storage elements), one or more input devices, and/or one or more output devices. The processor thus can access one or more input devices to obtain input data, and can access one or more output devices to communicate output data. The input and/or output devices can include one or more of the following: Random Access Memory (RAM), Redundant Array of Independent Disks (RAID), floppy drive, CD, DVD, magnetic disk, internal hard drive, external hard drive, memory stick, or other storage device capable of being accessed by a processor as provided herein, where such aforementioned examples are not exhaustive, and are for illustration and not limitation.

The computer program(s) can be implemented using one or more high level procedural or object-oriented programming languages to communicate with a computer system; however, the program(s) can be implemented in assembly or machine language, if desired. The language can be compiled or interpreted. The device(s) or computer systems that integrate with the processor(s) can include, for example, a personal computer(s), workstation (e.g., Sun, HP), personal digital assistant (PDA), handheld device such as cellular telephone, laptop, handheld, or another device capable of being integrated with a processor(s) that can operate as provided herein. Accordingly, the devices provided herein are not exhaustive and are provided for illustration and not limitation.

References to "a microprocessor" and "a processor", or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network using a variety of communications protocols, and unless otherwise specified, can be arranged to include a combination of external and internal memory devices, where such memory can be contiguous and/or partitioned based on the application. Accordingly, references to a database can be understood to include one or more memory associations, where such references can include commercially available database products (e.g., SQL, Informix, Oracle) and also proprietary databases, and may also include other structures for associating memory such as links, queues, graphs, trees, with such structures provided for illustration and not limitation.

Accordingly, other embodiments are within the scope of the following claims.

We claim:

1. A method of determining and displaying physiological information related to a heart surface, comprising:

for each of multiple, different catheter positions in a heart cavity, concurrently measuring cardiac beats in signals at one or more electrodes on a catheter in response to electrical activity in the heart cavity and collecting a plurality of additional data signals related to the cardiac beats;

computing criteria that is used to characterize beat morphology of a cardiac beat in the plurality of additional data signals, wherein the criteria are based on a comparison of the plurality of additional data signals and a beat template;

selecting a subset of less than all of the cardiac beats in the signals measured by the one or more electrodes by determining, based on the criteria, whether to select the cardiac beat and include beat data for the cardiac beat in the subset of less than all of the cardiac beats in the signals;

selecting cardiac beats from the subset of less than all of the cardiac beats in the signals by at least one of:
  comparing beat duration information for the cardiac beat with an expected beat duration and excluding the beat data for the cardiac beat if the beat duration is below a beat duration threshold, and
  selecting the beat data for the cardiac beat based on a location of the cardiac beat in a beat train of the cardiac beats;

determining the physiological information at multiple locations of an endocardium surface by processing the cardiac beats selected from the subset of less than all of the cardiac beats in the signals measured by the one or more electrodes;

displaying at least a portion of the determined physiological information on a display to aid physicians in determining a source of arrhythmias and in guiding therapeutic treatment; and guiding therapeutic treatment based on the determined physiological information.

2. The method of claim 1, comprising synchronizing the signals measured at the different catheter positions with one another based on the plurality of additional data signals.

3. The method of claim 1, wherein processing the cardiac beats selected from the subset of less than all of the cardiac beats in the signals measured by the one or more electrodes comprises processing the cardiac beats selected from the subset of less than all of the cardiac beats in the signals measured by the one or more electrodes as though they were obtained at one time.

4. The method of claim 1, wherein computing criteria comprises comparing one or more of the plurality of additional data signals for the cardiac beat with one or more templates representing an exemplary cardiac beat of interest.

5. The method of claim 4, wherein the computed criteria comprises a value representing a similarity between the one or more of the plurality of additional data signals for the cardiac beat and the one or more templates.

6. The method of claim 5, wherein selecting the subset of less than all of the cardiac beats in the signals comprises comparing the value with a threshold value and including the beat data for the cardiac beat in the subset of less than all of the cardiac beats in the signals if the value is greater than the threshold value.

7. The method of claim 1, wherein computing criteria and selecting the subset of less than all of the cardiac beats in the signals comprises:
  collecting one or more of the plurality of additional data signals from a plurality of channels;
  comparing each of the one or more of the plurality of additional data signals from the plurality of channels to associated templates to generate comparison results; and
  determining whether to include the beat data for the cardiac beat in the subset of less than all of the cardiac beats in the signals based on the comparison results.

8. The method of claim 1, wherein computing criteria and selecting the subset of less than all of the cardiac beats in the signals comprises:
  comparing beat duration information for the cardiac beat with an expected beat duration; and
  excluding the beat data for the cardiac beat from the subset of less than all of the cardiac beats in the signals if the beat duration is below a threshold.

9. The method of claim 1, wherein computing criteria and selecting the subset of less than all of the cardiac beats in the signals comprises:
  comparing an energy for the cardiac beat with an expected energy; and
  excluding the beat data for the cardiac beat from the subset of less than all of the cardiac beats in the signals if the energy is above a threshold.

10. The method of claim 1, wherein selecting the subset of less than all of the cardiac beats in the signals comprises selecting the beat data for the cardiac beat in the subset of less than all of the cardiac beats in the signals based on a location of the heart beat in a beat train of a morphology of interest.

11. A system for determining and displaying physiological information related to a heart surface, the system comprising:
  one or more electrodes configured to concurrently measure, for each of multiple, different catheter positions in a heart cavity, cardiac beats in signals in response to electrical activity in the heart cavity having the heart surface;
  one or more additional devices configured to measure a plurality of additional data signals related to the cardiac beats; and
  a processing unit configured to:
    define a template set comprising the plurality of additional data signals collected during an exemplary beat of interest;
    determine criteria that is used to characterize beat morphology of a cardiac beat in the plurality of additional data signals, wherein the criteria are based on a comparison of the plurality of additional data signals and the template set;
    select a subset of less than all of the cardiac beats in the signals measured by the one or more electrodes by determining, based on the criteria, whether to select the cardiac beat and include beat data for the cardiac beat in the subset of less than all of the cardiac beats in the signals;
    select cardiac beats from the subset of less than all of the cardiac beats in the signals by at least one of:
      comparing beat duration information for the cardiac beat with an expected beat duration and excluding the beat data for the cardiac beat if the beat duration is below a beat duration threshold, and
      selecting the beat data for the cardiac beat based on a location of the cardiac beat in a beat train of the cardiac beats;
    determine the physiological information at multiple locations of an endocardium surface by processing the cardiac beats selected from the subset of less than all of the cardiac beats in the signals measured by the one or more electrodes;
    display at least a portion of the determined physiological information on a display to aid physicians in determining a source of arrhythmias and in guiding therapeutic treatment and
    guide therapeutic treatment based on the determined physiological information.

12. The system of claim 11, wherein the processing unit is configured to provide at least one of a correlation of each of the plurality of additional data signals to the template set and alignment of the signals measured at the different positions relative to a phase in an electrical cycle of the heart.

* * * * *